(12) United States Patent
Meltzer et al.

(10) Patent No.: US 6,525,206 B1
(45) Date of Patent: Feb. 25, 2003

(54) COMPOUNDS WITH HIGH MONOAMINE TRANSPORTER AFFINITY

(75) Inventors: Peter C. Meltzer, Lexington, MA (US); Paul Blundell, Winchester, MA (US); Pinglang Wang, Cambridge, MA (US); Bertha K. Madras, Newton, MA (US)

(73) Assignees: President and Fellows of Harvard College, Cambridge, MA (US); Organix, Inc., Woburn, MA (US)

( * ) Notice: Subject to any disclaimer, the term of this patent is extended or adjusted under 35 U.S.C. 154(b) by 0 days.

(21) Appl. No.: 09/691,396

(22) Filed: Oct. 17, 2000

(51) Int. Cl.$^7$ ............................................. C07D 315/00
(52) U.S. Cl. ...................................................... 549/427
(58) Field of Search ........................................ 549/427

(56) References Cited

FOREIGN PATENT DOCUMENTS

WO     WO 98/06689     2/1998

OTHER PUBLICATIONS

Ghosh, et al, 2000, Tetrahedron Letters, 41(44), 8425–8429.*
Acton, et al., "Single–photon emission tomography imaging of serotonin transporters in the nonhuman primate brain with [$^{123}$I]ODAM", European Journal of Nuclear Medicine, vol. 26, No. 10, pp. 1359–1362, Oct. (1999).
Biederman, M.D., "Attention–Deficit/Hyperactivity Disorder: A Life Span Perspective", J. Clin, Psychiatry, 59:4–16, (1998).
Bogeso, et al., "3–Phenyl–1–indanamines. Potential Antidepressant Activity and Potent Inhibition of Dopamine, Norepinephrine, and Serotonin Uptake", J. Med. Chem, 28, pp. 1817–1828, (1985).
Canfield, et al., "Autoradiographic Localization of Cocaine Binding Sites by [$^3$H]CFT ([$^3$H]WIN 35,428) in the Monkey Brain", Synapse 6, pp. 189–195, (1990).
Coyle, et al., Catecholamine Uptake by Synaptosomes in Homogenates of Rate Brain: Stereospecificity in Different Areas, The Journal of Pharmacology and Experimental Therapeutics, vol. 170, No. 2, (1969).
Cyr, et al., "Current Drig Therapy Recommendations for the Treatment of Attention Deficit Hyperactivity Disorder, Drugs", Aug.: 56 (2) pp. 215–223, (1998).
Ficini, "Laboratoire de Chimie Structurale, Faculte des Sciences, Paris", 5$^e$, J.Bull. Soc. Chim Fr. Pp119–124, (1956).
Fischman, et al., "Rapid Detectionof Parkinson's Disease by SPECT With Altropane: A Selective Ligand for Dopamine Transporters, Synapse 29:128–141", (1998).
Gehlert, et al., "The Selective Noreppinephrine Reuptake Inhibitor, LY368975, Reduces Food Consumption in Animal Models of Feeding, The Journal of Pharmacology and Experimental Therapeutics", vol. 287, No. 1, pp. 127–127, (1998).

Giros, et al., "Hyperlocomotion and indeifference to cocaine and amphetamine in mice lacking the dopamine transporter", Nature, vol. 379, pp. 606–612, (1996).
Hadrich, et al., "Synthesis and Characterizationof Flourescent Ligands for theNorepinephrine Transporter: Potential Neuroblastoma Imaging Agents", J. Med. Chem., vol. 42, pp. 3101–3108, (1999).
Heinz, et al., "Reduced Central Serotonin Transporters in Alcoholism, American Journal of Psychiatry", vol. 155, pp. 1544–1549, (1998).
Jorenby, et al., "A Controlled Trial of Sustained–Release Bupropion, A Nicotine Patch, or Both for Smoking Cessation", The New England Journal of Medicine, vol. 340, pp. 685–691, (1999).
Hirschfeld, M.D., "Care of the Sexually Active Depressed Patient", J. Clin. Psychiatry, vol. 60, pp. 32–35, (1999).
Kaufman, et al., "Severe Depletion of Cocaine Recognition Sites Associated With the Dopamine Transporter I Parkinson's Diseased Striatum", Synapse, 9:43–49, (1991).
Kung, H.F., "Synthesis of New Bis(aminoethanethiol) (BAT) Derivatives: Possible Ligands for $^{99m}$Tc Brain Imaging Agents", J. Med. Chem., vol. 28, pp. 1280–1284, (1985).
Madras, et al., "Cocaine Receptors Labeled by [$^3$H] 2β–Carbomethoxy–3β–(4–flurorphenyl)tropane, molecular Pharmacology", vol. 36, 518–524, (1989).
Madras, et al., "Technepine: A High–Affinity $^{99m}$Technetium Probe to Label the Dopamine Transporter in Brain by SPECT Imaging", Synapse 22, pp. 239–245 (1996).
Madras, et al., "Nitrogen–Based Drugs Are Not Essential for Blockade of Monoamine Transporters", Synapse, 24:340–348, (1996).
Malison, et al., "Reduced Brain Serotonin Transporter Availability in Major Depression as Measured by [$^{123}$I]– 2β–carbomethoxy–3β–(4–iodophenyl)tropane and Single Photon Emission Computed Tomography", Biological Psychiatry, vol. 44, No. 10, pp. 1090–1098, (1998).
McAfee, et al., "Sustained Release Buoropioin for smoking Cessation", New Englanf Journal of Medicine, vol. 338, No. 9, 619, (1998).

(List continued on next page.)

*Primary Examiner*—Joseph K. McKane
*Assistant Examiner*—Andrea D Small
(74) *Attorney, Agent, or Firm*—Edwards & Angell, LLP; George W. Neuner; Cara Z. Lowen

(57) ABSTRACT

Featured compounds have high monoamine transport affinity and are characterized by one of the following two general formulas set out above. The compounds bind selectively or non-selectively to monoamine transporters. The compounds are useful to treat various medical indications including attention deficit hyperactivity disorder (ADHD), Parkinson's disease, cocaine addiction, smoking cessation, weight reduction, obsessive-compulsive disorder, various forms of depression, traumatic brain injury, stroke, and narcolepsy.

7 Claims, No Drawings

OTHER PUBLICATIONS

McCann, U.D., "Positron emission tomographic evidence of toxic effect of MDMA ("Ectstasy") on brain serotonin neurons in human beings", The Lancet, vol. 352, pp. 1433–1437, (1998).

O'Neil, et al., "Preparation and Structural Characterization of Monoamine–Monamide Bis(thiol) Oxo Complexes of Technetium (V) and Rhenium(V), Inorganic Chemistry", vol. 33, No. 2, pp. 319–323, (1994).

O'Neil, et al., "Progestin Radiopharmaceuticals Labled with Technetium and Rhenium: Synthesis, Binding Affinity, and in Vivo Distribution of a New Progestin $N_2S_2$–Metal Cinjugate, Bioconjugate", Chem., 5, pp. 189–193, (1994).

Oya, et al., "A New Single–Photon Emission Computed Tomography Imaging Agent for Serotonin Transporters: [$^{123}$I]IDAM, 5–Iodo–2–((2–((dimethylamino)methyl)–phenyl)thio)benzyl Alcohol", Journal of Medicinal Chemistry, vol. 42, No. 3, pp. 333–335, (1999).

Raffel, et al., "Influence of Vesicular Storage and Monoamine Oxidase Activity on [$^{11}$C]Phenylephrine Kinetics: Studies in Isolated Rat Heart", The Journal of Nuclear Medicine, vol. 40, No. 2, pp. 323–330, (1999).

Riggs, et al., "An Open Trial of Bupropion for ADHD in Adolescents With Substance Use Disorders and Conduct Disorder, Journal of the American Academy of Child & Adolescent Phychiatry", 37:12 pp. 1271–1278, (1999).

Seeman, et al., "Anti–hyperactivity medication: Methylphenidate and amphetamine", Molecular Psychiatry, 3:386–396, (1998).

Seibyl, et al., "Decreased Single–Photon Emission Computed Tomograpic [$^{123}$I]β–CIT Striatal Uptake Correlates with Symptom Severity in Parkinson's Disease, Annals of Neurology", vol. 38, No. 4, pp. 589–598, (1995).

Semple, et al., "Reduced in vivo binding to the serotonin transporter in the cerebral cortex of MDMA ('ecstacy') users, The British Journal of Psychiatry", vol. 175, pp. 63–69, (1999).

Szabo, et al., "Kinetic Analysis of [$^{11}$C]McN5652: A Serotonin Transporter Radioligand", Journal of Cerebral Blodd Flow and Metabolism, 19:967–981, (1999).

Bogeso, et al., Journal of Medicinal Chemistry, vol. 28, No. 12, Dec. 1985 (Dec. 1985), pp. 1817–1828.

Basalf, et al., International Journal of Chemistry, vol. 6, No. 3, 1995, pp. 55–65 (XP002209431) –Abstract.

Muller, et al., Journal of Organic Chemistry, vol. 16, No. 7, Jul. 1951 (Jul. 1951), pp. 1003–1024 (XP002209565).

Corson, et al. Journal of Organic Chemistry, vol. 27, No. 5, May 1962 (May 1962), pp. 1636–1640 (XP002209566).

Zwiebrak, et al. Journal of Organic Chemistry, vol. 28, No. 12, Dec. 1963 (Dec. 1963), pp. 3392–3399 (XP002209563).

Walter, et al. Journal of Medicinal Chemistry, vol. 17, No. 4, Apr. 1974 (Apr. 1974), pp. 459–463 (XP 002209564).

McOmie, et al. Tetrahedron, vol. 24, No. 5, Mar. 1968 (Mar. 1968), pp. 2289–2292 (XP000567035).

Breslow, et al. Journal of Organic Chemistry, vol. 26, No. 3, Mar. 1961 (Mar. 1961), pp. 679–681 (XP002209567).

* cited by examiner

COMPOUNDS WITH HIGH MONOAMINE TRANSPORTER AFFINITY

FEDERALLY SPONSORED RESEARCH OR DEVELOPMENT

The U.S. Government may have certain rights in this invention pursuant to Grant Nos. NIDA RO1 DA11542; NIDA NO1 DA7-8081; DA 06303; and DA 11558 awarded by NIDA (NIH).

TECHNICAL FIELD

This invention relates to novel compositions with affinity for a monoamine transporter, such as the dopamine, norepinephrine, or serotonin transporter, in brain and in peripheral tissues.

BACKGROUND

Monoamine transporters play a variety of roles, and compounds with affinity for the monoamine transporters have been proposed for therapy and/or diagnosis of medical indications that include (but are not limited to) attention deficit hyperactivity disorder (ADHD), Parkinson's disease, cocaine addiction, smoking cessation, weight reduction, obsessive-compulsive disorder, various forms of depression, traumatic brain injury, stroke, and narcolepsy.

The dopamine transporter (DAT) in particular is a primary mechanism for terminating the effects of synaptic dopamine and maintaining homeostatic levels of extracellular dopamine in brain. Giros et al., *Nature* 379: 696–612 (1996). The dopamine transporter is a principal target of therapeutic and psychostimulant drugs of abuse. For example, the dopamine transporter is an important target of drugs (including methylphenidate, pemoline, amphetamine and bupropion) used to treat ADHD. Seeman and Madras, *Mol. Psychiatry* 3:386–396 (1998); Cyr and Brown, *Drugs*, 56:215–223 (1998); Biederman, J. Clin. Psychiatry 59: 4–16 (1998); Riggs et al., *J. Am Acad. Child Adolesc. Psychiatry* 37:1271–1278 (1999). The dopamine transporter is also a principal target of brain imaging agents used, for example, diagnostically.

It has been suggested that the therapeutic benefit of benztropin (Cogenting) for Parkinson's disease results in part from blocking dopamine transport thereby increasing synaptic dopamine. Coyle and Snyder, *J. Pharmacol. Exp. Ther.*,170:221–319 (1969).

The antidepressant bupropion apparently is also a monoamine transport inhibitor [Hirschfeld, *J. Clin. Psychiatry* 17:32–35 (1999)], and it has been suggested as a treatment to aid smoking cessation. Jorenby et al., *N. Engl. J Med.*, 340:685–691 (1999); McAfee et al., *N. Engl. J. Med.*, 338:619 (1998).

The dopamine transporter has been identified as an effective marker for dopamine terminals in Parkinson's disease. Kaufman and Madras, *Synapse* 9: 43–49 (1991). Brain imaging of the transporter in humans with Parkinson's disease and in animals with experimentally produced Parkinsonism has confirmed the usefulness of the dopamine transporter in this application. Fischman et al., Synapse 29: 128–141, 1998, Seibyl et al., *Ann. Neurol.* 38:589–598.

The serotonin transporter (SERT) regulates extracellular serotonin levels. It is a principal target of effective drugs (known as serotonin-selective reuptake inhibitors or SSRI's) used to treat melancholic depression, atypical depression, dysthymia and obsessive-compulsive disorder. It also is a conduit of entry into serotonin containing neurons of neurotoxic substituted amphetamines. Selective imaging agents that label the serotonin transporter would be useful to investigate the status of the transporter in depression [Malison et al. *Bio. Psychiatry* 44:1090–1098 (1998)], alcoholism [Heinz et al. *Am. J. Psychiatry* 155:1544–1549 (1998)], obsessive-compulsive disorder, and substituted amphetamine abusers [McCann et al., *Lancet* 352:1433–1437 (1998); Semple et al., *Br., J. Psychiatry* 175: 63–39 (1999)]. There are various reports generally dealing with individual serotonin transporter imaging agents. Acton et al. *Eur. J. Nucl. Med.* 26:1359–1362 (1999); Szabo et al. *J. Cereb. Blood Flow Metab.* 19:967–981 (1999); Oya et al. *J. Med Chem.* 42:333–335 (1999).

Norepinephrine regulates mood, is involved in learning and memory, and controls endocrine and autonomic functions. Dysfunction of norepinephrine neurotransmission has been implicated in depression, cardiovascular and thermal pathophysiology. The norepinephrine transporter (NET) regulates extracellular levels of norepinephrine in brain, in heart, and in the sympathetic nervous system. Clinically, the norepinephrine transporter is a principal target of selective or non-selective anti-depressant drugs and stimulant drugs of abuse such as cocaine and amphetamines. Blockade of the norepinephine transporter is implicated in appetite suppression. Gehlert et al. *J. Pharmacol. Exp. Ther.* 287:122–127 (1998). Imaging of the norepinephrine transporter may also be useful for viewing the status of sympathetic innervation in the heart and in other adrenergic terminals, and for detecting neuroblastomas. Hadrich et al. *J. Med. Chem.* 42:3010–3018 (1999); Raffel et al., *J. Nucl. Med.* 40:323–330 (1999).

It is desirable to avoid unwanted side effects of treatments targeting monoamine transporters, to the extent possible: It is also desirable to produce efficient and effective diagnostics for various conditions involving monoamine transporters.

SUMMARY

The invention features compounds of two general classes that have high and selective monoamine transport affinity. Featured compounds of the first class (which we term oxaindanes) generally have the following formula:

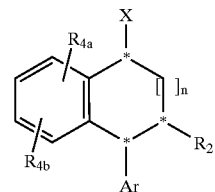

WHERE:
* indicates a chiral center, and each chiral center, independently, may be R, S, or R/S.
—X=—CH$_2$R$_1$; —CHR$_1$R$_5$; —CR$_1$=O; —CR$_6$=O; —O—R$_1$; —SR$_1$; —SOR$_6$; —SO$_2$R$_6$; —SO$_2$NHR$_1$; or —CH=CR$_1$R$_5$ and where:
  a. —R$_1$ and —R$_5$ are independently selected from: —H; —CH$_3$; —CH$_2$CH$_3$; or —CH$_2$(CH$_2$)$_m$CH$_3$, where m=0, 1, 2, or 3; PROVIDED THAT, when X=—O—R$_1$, then R$_1$≠H; and
  b. —R$_6$ is 'selected from: —OH; —OCH$_3$; —NHR$_1$; —O-alkyl; —O-alkenyl; —O-alkynyl; —O-allyl; —O-iodoallyl; -alkyl; -alkenyl; -alkynyl; -allyl; -isopropyl; and -isobutyl.

—Ar=either
  a) phenyl substituted at any two positions with $R_{3a}$ and $R_{3b}$, where $R_{3a}$ and $R_{3b}$ are as defined in options "I." or "II.", below; or
  b) 1-napththyl or 2-naphthyl, substituted at any two positions with $R_{3a}$, and $R_{3b}$ where $R_{3a}$ and $R_{3b}$ are as defined in option "I.", below);
    OPTION I for $R_{3a}$, and $R_{3b}$ (phenyl or naphthyl substitutions)
      —$R_{3a}$ and —$R_{3b}$ are independently selected from: —H; —Br; —Cl; —I; —F; —H; —OCH$_3$; —CF$_3$; —NO$_2$; —NH$_2$; —CN; —NHCOCH$_3$, —C(CH$_3$)$_3$, —(CH$_2$)$_q$CH$_3$ where q=0–6; —COCH$_3$; —F (at the 2, 3 or 4 position), —Cl (at the 2, 3 or 4 position); —I (at the 2, 3 or 4 position); alkyl; alkenyl; alkynyl; allyl; iospropyl; isobutyl; alkyl; -alkylN$_2$S$_2$chelator; -alkylN$_2$S$_2$Tc chelator, such that N$_2$S$_2$ is part of a chelating moiety such as those known in the art which contain two nitrogens and two sulfur atoms, in addition to carbon and optionally other heteroatoms, see, for example, O'Neil et al., *Bioconjugate Chem.* 5:182–193 (1994); O'Neil et al., *Inorg. Chem.* 33:319–323 (1994); Kung et al., *J. Nucl. Med.* 27:1051 (1986); Kung et al., *J. Med. Chem.* 28: 1280–1284 (1985), hereby incorporated by reference; or COR$_7$, where R$_7$ is defined below;
        OR
    OPTION II. for $R_{3a}$, and $R_{3b}$ (phenyl substitutions)
      —$R_{3a}$ and —$R_{3b}$ as a pair are independently selected from the following pairs: 3,4-diCl; 3,4, diOH; 3,4-diOAc; 3,4-diOCH$_3$; 3-OH,4-Cl; 3-OH,4-F; 3-Cl,4-OH; or 3-F,4-OH;

n=0 or 1;

—$R_2$=—COOCH$_3$; —COR$_7$; -alkyl; -alkenyl; -allyl; -iodoallyl; -alkynyl; -isoxazole; -oxadiazole; -oxazole; -alkylN$_2$S$_2$ chelator, —O-alkylN$_2$S$_2$ chelator. -alkylN$_2$S$_2$Tc chelator; —O-alkylN$_2$S$_2$Tc chelator; where,
  —R$_7$ is —HR$_8$; morpholinyl; piperidinyl; —CH$_3$; —CH$_2$CH$_3$; —CH$_2$(CH$_2$)$_r$CH$_3$ where r=0, 1, 2, or 3; alkyl; alkenyl; alkynyl; allyl; isopropyl; iodoallyl; O-iodoallyl; -isobutyl; —CH$_2$SO$_2$; -alkylN$_2$S$_2$ chelator; -alkylN$_2$S$_2$Tc chelator; O-alkylN$_2$S$_2$ chelator, or —O-alkylN$_2$S$_2$Tc chelator; and —R$_8$ is -alkyl; -alkenyl; -allyl; iodoallyl; -alkynyl; -isoxazole; -oxadiazole; -oxazole; -alkylN$_2$S$_2$ chelator; —O-alkylN$_2$S$_2$ chelator, -alkylN$_2$S$_2$Tc chelator; —O-alkylN$_2$S$_2$Tc chelator.

Preferred substituents for the above general formula are as follows: n is preferably 0; X is preferably —O—R$_1$, where R$_1$ is preferably —CH$_3$; Ar is preferably phenyl or napthyl (1- or 2-napthhyl), substituted at any two positions with $R_{3a}$, and $R_{3b}$; e.g., $R_{3a}$ and $R_{3b}$ may independently be —Cl, —H. Particularly preferred compounds are O-1617; O-1630; O-1833; O-1925, described below in Table 1.

The second general class of compounds (which we generally term tetrahydropyranyl esters or THP esters) generally have one of the following three formulas:

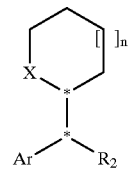

A

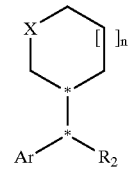

B

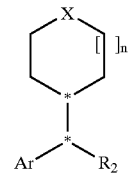

C

WHERE:
  n is 0, 1, 2, or 3;
  >X is >CH$_2$; >CHY; >C(Y,Z); >C=O; >O; >S; >SO; >SO$_2$; >NSO$_2$; >NSO$_2$R$_3$; or >C=CYZ;
    where Y and Z are independently selected from H; Br; Cl; I; F; OH; OCH$_3$; CF$_3$; NO$_2$; NH$_2$; CN; NHCOCH$_3$; N(CH$_3$)$_2$; (CH$_2$)$_m$CH$_3$, where m=0–6; COCH$_3$; alkyl, alkenyl, alkynyl, allyl, isopropyl, isobutyl;
  —Ar=either
    a) phenyl substituted at any two positions with $R_{1a}$ and $R_{1b}$, where $R_{1a}$ and $R_{1b}$ are as defined in options "I." or "II.", below; or
    b) 1-napththyl or 2-naphthyl, substituted at any two positions with $R_{1a}$ and $R_{1b}$ where $R_{1a}$ and $R_{1b}$ are as defined in option "I.", below);
    OPTION I for $R_{1a}$, and $R_{1b}$ (phenyl or naphthyl substitutions)
      —$R_{1a}$ and —$R_{1b}$ are independently selected from: —H; —Br; —Cl; —I; —F; —OH;—OCH$_3$; —CF$_3$; —NO$_2$; —NH$_2$; —CN; —NHCOCH$_3$, —C(CH$_3$)$_3$, —(CH$_2$)$_q$CH$_3$ where q=0–6; —COCH$_3$; —F (at the 2, 3 or 4 position), —Cl (at the 2, 3 or 4 position); —I (at the 2, 3 or 4 position); alkyl; alkenyl; alkynyl; allyl; iospropyl; isobutyl; -alkylN$_2$S$_2$ chelator, -alkylN$_2$S$_2$Tc chelator; or COR$_4$, where R$_4$ is defined below;
        OR
    OPTION II. for $R_{1a}$, and $R_{1b}$ (phenyl substitutions)
      —$R_{1a}$ and —$R_{1b}$ as a pair are independently selected from the following pairs: 3,4-diCl; 3,4, diOH; 3,4-diOAc; 3,4-diOCH$_3$; 3-OH, 4-Cl; 3-OH, 4-F; 3-Cl, 4-OH; or 3-F, 4-OH;
  —$R_2$=—COOCH$_3$; —COR$_4$; -alkyl; -alkenyl; -allyl; -iodoallyl; alkynyl; -isoxazole; -oxadiazole; -oxazole; -alkylN$_2$S$_2$ chelator; —O-alkylN$_2$S$_2$ chelator. -alkylN$_2$S$_2$Tc chelator; —O-alkylN$_2$S$_2$Tc chelator; where,
    —R$_4$ is=—NHR$_5$; morpholinyl; piperidinyl; —CH$_3$; —CH$_2$CH$_3$; CH$_2$(CH$_2$)$_r$CH$_3$ where r=0, 1, 2, or 3; alkyl; alkenyl; alkynyl; allyl; isopropyl; iodoallyl; O-iodoallyl; -isobutyl; —CH$_2$SO$_2$; -alkylN$_2$S$_2$ chelator, -alkylN$_2$S$_2$Tc chelator; O-alkylN$_2$S$_2$ chelator; or —O-alkylN$_2$S$_2$Tc chelator; and —R$_5$ is= -alkyl; -alkenyl; -allyl; -iodoallyl; -alkynyl; -isoxazole; -oxadiazole; -oxazole; -alkylN$_2$S$_2$ chelator; —O-alkylN$_2$S$_2$ chelator; -alkylN$_2$S$_2$Tc chelator; —O-alkylN$_2$S$_2$Tc chelator.

Preferred compounds are those with the following substituents: X is preferably O; n is preferably 1; preferably the compound has formula A, above; R$_2$ is preferably —COR$_4$, most preferably —COOCH$_3$; —Ar is preferably phenyl substituted at any two positions with R$_{3a}$, and R$_{3b}$, e.g., where R$_{3a}$, and R$_{3b}$ are independently selected from —H and Cl. R$_4$ is —OCH$_3$ or —C$_2$H$_5$. Particularly preferred compounds are compounds: 1a (compound O-1793), 1b (compound O-1792), 2a (compound O-1794), 2b (compound O-1783), and the corresponding carboxylic acids, 3a, 3b, 4a, or 4b.

Compounds of the above formula which demonstrate monoamine transport affinity are useful for labeling receptor-expressing cells using in vitro techniques that are generally known to those skilled in the field and are generally described below. They may also be used for in vivo imaging in the conditions described above and to treat various medical indications, including attention deficit hyperactivity disorder (ADHD), Parkinson's disease, cocaine addiction, smoking cessation, weight reduction, obsessive-compulsive disorder, various forms of depression, traumatic brain injury, stroke, and narcolepsy.

The invention also includes methods of making medicaments for treating the above indications, as well as pharmaceutical compositions comprising the compounds formulated to treat those indications, e.g., with a pharmaceutically acceptable carrier.

The details of one or more embodiments of the invention are set forth in the accompanying structures and the description below. Other features, objects, and advantages of the invention will be apparent from the following description and structures, and from the claims.

DETAILED DESCRIPTION

The compounds according to the invention are detailed above and in the claims. Formulation into pharmaceuticals, and use of those pharmaceuticals are detailed below. In therapeutic applications, the compound may be administered with a physiologically acceptable carrier, such as physiological saline. The therapeutic compositions of the invention can also contain a carrier or excipient, many of which are known to skilled artisans. Excipients that can be used include buffers (e.g., citrate buffer, phosphate buffer, acetate buffer, and bicarbonate buffer), amino acids, urea, alcohols, ascorbic acid, phospholipids, proteins (e.g., serum albumin), EDTA, sodium chloride, liposomes, mannitol, sorbitol, and glycerol. The compounds of the invention can be formulated in various ways, according to the corresponding route of administration. For example, liquid solutions can be made for ingestion or injection; gels or powders can be made for ingestion, inhalation, or topical application. Methods for making such formulations are well known and can be found in, for example "Remington's Pharmaceutical sciences."

Routes of administration are also well known to skilled pharmacologists and physicians and include intraperitoneal, intramuscular, subcutaneous, rectal and intravenous administration. Additional routes include intracranial (e.g., intracisternal or intraventricular), intraorbital, opthalmic, intracapsular, intraspinal, intraperitoneal, transmucosal, topical, subcutaneous, and oral administration. It is expected that the oral route will be preferred for the administration of the compounds. The subcutaneous route may also be used. Another route of administration of the compounds that is feasible is the intraperitoneal route. Systemic administration of the compounds can also be effective. Thus, while one may target the compounds more specifically to their site of action, such targeting is not necessary for effective treatment.

It is well known in the medical arts that dosages for any one patient depend on many factors, including the general health, sex, weight, body surface area, and age of the patient, as well as the particular compound to be administered, the time and route of administration, and other drugs being administered concurrently. Dosages for the compound of the invention will vary, but can, when administered intravenously, be given in doses of approximately 0.01 mg to 100 mg/ml blood volume. A dosage can be administered one or more times per day, if necessary, and treatment can be continued for prolonged periods of time, up to and including the lifetime of the patient being treated. If a compound of the invention is administered subcutaneously, the dosage can be reduced, and/or the compound can be administered less frequently. Determination of correct dosage for a given application is well within the abilities of one of ordinary skill in the art of pharmacology. In addition, those of ordinary skill in the art can turn to data and experiments presented below for guidance in evaluating the binding properties of compounds, e.g., when developing an effective treatment regime. Additionally, one could begin tailoring the dosage of the compounds required for effective treatment of humans from the dosage proven effective in the treatment of small mammals. Routine experimentation would be required to more precisely define the effective limits of any given administrative regime. For example, in a conservative approach, one could define the lowest effective dosage in small mammals, and administer that dose to progressively larger mammals before beginning human safety trials.

I. SYNTHESIS OF OXAINDANES

The following general description relates to the synthesis of the oxaindane analogs.

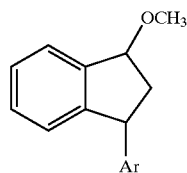

CIS- AND TRANS-1-METHOXY-3-ARYL-INDANS

The general synthesis of the 3-aryl substituted oxaindanes was accomplished via the route presented in the scheme for the 3-naphthyl analogs shown below. The synthesis of the four isomers (two diastereomers 7 and 10, and a pair of enantiomers of each, a and b), was accomplished via an intermediate described by Bøgesø, K. P.et al., *J. Med. Chem.* 28, 1817–1828 (1985). Thus, the cis diastereomers 6a and 6b were prepared in five steps from 2-bromobenzaldehyde. These cis alcohols 6a and 6b were then methylated with sodium hydride and methyl iodide to provide the target cis-methoxyindans 7a and 7b. Inversion of stereochemistry at the C-1 position was accomplished via Mitsunobu inversion by reaction with benzoic acid in the presence of triphenyl phosphine and diethylazodicarboxylate to provide the trans enantiomers 8a and 8b (only one enantiomer is shown in the scheme). Methylations, as for alcohols 6a and 6b, then provided the target trans-methoxyindans 10a and 10b.

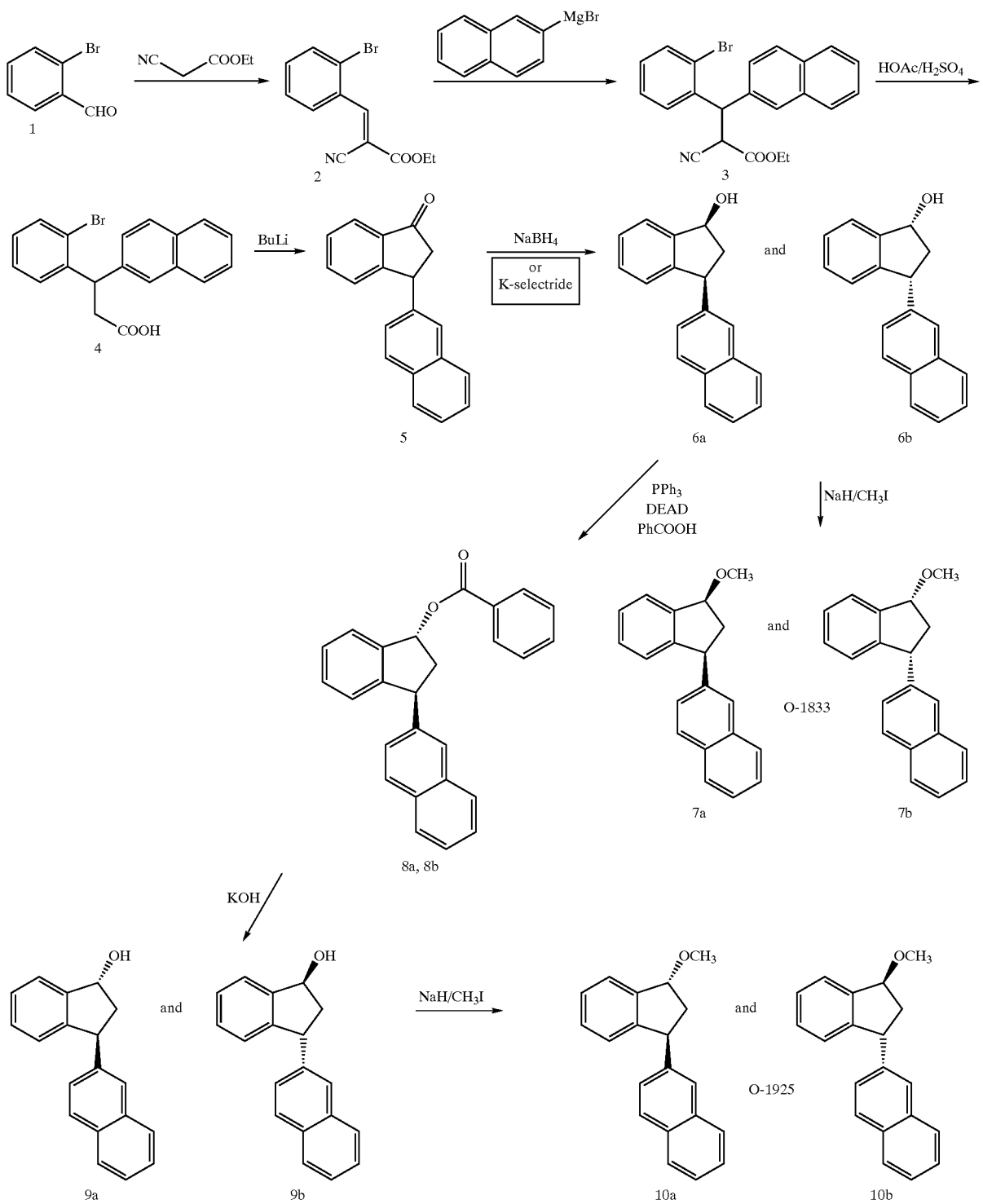

Experimental Section

Experimental details for the above general synthesis follow.

NMR spectra were recorded in CDCl$_3$ on a JEOL 300 NMR spectrometer operating at 300.53 MHz for $^1$H, and 75.58 MHz for $^{13}$C. TMS was used as internal standard. Melting points are uncorrected and were measured on a Gallenkamp melting point apparatus. Thin layer chromatography (TLC) was carried out on Baker Si250F plates. Visualization was accomplished with either UV exposure or treatment with phosphomolybdic acid (PMA). Flash chromatography was carried out on Baker Silica Gel 40 mM. Elemental analyses were performed by Atlantic Microlab, Atlanta, Ga. All reactions were conducted under an inert (N$_2$) atmosphere.

Ethyl 2-cyano-3-(2-bromophenyl)-2-propenoate, 2.

2-Bromobenzaldehyde 1 (10.0 g, 54.0 mmol), ethyl cyanoacetate (6.91 g, 61.1 mmol) and piperidine (0.11 mL, 1.08 mmol) in toluene (45 mL) were refluxed at 135° C. with a Dean-Stark trap for 3 h. The solvent was removed on a rotary evaporator. The residue was crystallized from isopropyl ether to give 2 as a white powder (12.0 g, 75%): $R_f$ 0.3 (10% EtOAc/hexanes); $^1$H—NMR (CDCl$_3$) δ 8.63 (s, 1H), 8.17 (dd, 1H, J=8, 2 Hz), 7.70 (dd, 1H, J=8, 1 Hz), 7.35–7.49 (m, 2H), 4.32 (q, 2H, J=7 Hz), 1.41 (t, 3H, J=7 Hz).

Ethyl 3-(2-bromophenyl)-3-(2-naphthyl)-2-cyanopropanoate, 3.

Magnesium (90 mg, 3.66 mmol) was added into a solution of 2-bromonaphthalene (0.76 g, 3.66 mmol) and dibromoethane (37 µL, 0.43 mmol) in THF (15 mL). The reaction was stirred at room temperature for 30 min, and 1 h at 70° C. The reaction was then cooled to room temperature, followed by the addition of ethyl 2-cyano-3-(2-bromophenyl)-2-propenoate, 2 (1.00 g, 3.05 mmol). The reaction mixture was then refluxed at 70° C. overnight. 3N HCl (3 mL) and H$_2$O (5 mL) were added dropwise. The water layer was extracted with ether (3×30 mL). The organic solvent was removed on a rotary evaporator. The residue was purified by flash chromatography (20% EtOAc/hexanes) to afford 0.87 g (63%) of 3 as a colorless oil: $R_f$ 0.46 (10% EtOAc/hexanes); $^1$H-NMR (CDCl3) δ 7.72–7.96 (m, 4H), 7.63 (td, 1H, J=9, 1 Hz) 7.24–7.52 (m, 5H), 7.1–7.2 (m, 1H), 5.45–5.49 (m, 1H), 4.40 (dd, 1H, J=12, 8 Hz), 4.01–4.21 (m, 2H), 1.08 (dt, 3H, J=22, 7 Hz).

3-(2-Bromophenyl)-3-(2-naphthyl)propanoic acid, 4.

Ethyl 3-(2-bromophenyl)-3-(2-naphthyl)-2-cyanopropanoate, 3 (0.84 g, 1.84 mmol), glacial acetic acid (10 mL), conc. H$_2$SO$_4$ (5 mL), and H$_2$O (5 mL) were refluxed at 100° C. for 24 h. The reaction mixture was poured into ice and extracted with EtOAc (2×40 mL). The organic solvent was removed on a rotary evaporator. The crude solid was stirred in 3M KOH (5 mL) for 30 min. The basic aqueous solution was extracted with CHCl$_3$ (3×10 mL). The basic aqueous solution was acidified with 3N HCl to pH4. The acidic solution was then extracted with EtOAc (3×20 mL). The organic solvent was removed on a rotary evaporator to give 4 (0.47 g, 72%) as a white solid: $R_f$ 0.4 (40% EtOAc/hexanes); $^1$H-NMR (CDCl$_3$) δ 7.69–7.79 (m, 4H), 7.54 (dd, 1H, J=8, 1 Hz), 7.40–7.48 (m, 2H), 7.33 (dd, 1H, J=9, 2 Hz), 7.17–7.25 (m, 2H), 7.02–7.08 (m, 1H), 5.18 (t, 1H, J=8 Hz), 3.13 (d, 2H, J=8 Hz).

3-(2-Naphthyl)indanone, 5.

n—BuLi (2.5 M in hexane, 1.2 mL, 2.91 mmol) was added dropwise into a solution of 3-(2-bromophenyl)-3-(2-naphthyl) propanoic acid, 4 (0.47 g, 1.32 mmol) at −10° C. The reaction mixture was stirred at 0° C. in an ice bath for 4h. 3N HCl (2 mL) and H$_2$O (3 mL) were added. The H$_2$O layer was extracted with ether (3×20 mL). The organic solvent was removed on a rotary evaporator. The residue was purified by flash chromatography (20% EtOAc/hexanes) to afford 5 (155 mg, 45%) as a colorless oil: $R_f$ 0.46 (10% EtOAc/hexanes); $^1$H-NMR (CDCl$_3$) δ 7.84 (d, 1H, J=8 Hz), 7.71–7.77 (m, 3H), 7.62 (d, 1H, J=1 Hz), 7.36–7.52 (m, 4H), 7.22 (dd, 1H, J=8, 1 Hz), 7.08 (dd, 1H, J=8, 2 Hz), 4.66 (q, 1H, J=4 Hz), 3.23 (dd, 1H, J=19, 8 Hz), 2.74 (dd, 1H, J=19, 4 Hz).

Cis-3-(2-Naphthyl)indan-1-ol, 6a and 6b.

K-Selectride (1M in THF, 1.20 mL, 1.20 mmol) was added into a solution of 3-(2-naphthyl)indanone, 5 (155 mg, 0.60 mmol) at 0° C. The reaction was stirred at 0° C. for 4h. H$_2$O (5 mL) was added and the reaction mixture was extracted with ether (3×20 mL). Ether was removed on a rotary evaporator. $^1$H-NMR of the crude residue confirmed the structure. The crude residue was used for next step without further purification.

Cis-3-(2-Naphthyl)-0-methylindanol, 7a and 7b.

Sodium hydride (60% dispersion, 80 mg, 2.15 mmol) was added into a solution of cis-3-(2-naphthyl)-indan-1-ol 6a and 6b (140 mg, 0.538 mmol) and methyl iodide (0.13 mL, 2.15 mmol) in THF (3 mL). The reaction mixture was stirred overnight. H$_2$O (4 mL) was added and the reaction mixture was extracted with ether (3×20 mL). The organic solvent was removed on a rotary evaporator. The residue was purified by flash chromatography (10% EtOAc/hexanes) to afford 0.10 g (68%) of 7a and 7b as a colorless oil: $R_f$ 0.57 (10% EtOAc/hexanes); $^1$H-NMR (CDCl$_3$) δ 7.75–7.80 (m, 3H), 7.71 (s, 1H), 7.38–7.58 (m, 3H), 7.25–7.32 (m, 2H), 7.20 (td, 1H, J=7, 1 Hz), 6.93 (d, 1H, J=7 Hz), 4.95 (t, 1H, J=7 Hz), 4.34 (t, 1H, J=8 Hz), 3.5 (s, 3H), 2.99 (qd, 1H, J=7, 6 Hz), 2.09 (qd, 1H, J=7, 6 Hz).

Trans-Benzoic acid 3-(2-naphthyl)indan-1-yl Esters, 8a and 8b.

Triphenylphosphine (1.44 g, 5.49 mmol) and benzoic acid (0.60 g, 4.91 mmol) were added to a solution of cis-3-(2-naphthyl)-indan-1-ol, 6a and 6b (0.645 g, 2.48 mmol) in anhydrous THF (20 mL). The reaction was treated dropwise with a solution of DEAD in THF (4.95 M, I mL) then stirred under nitrogen atmosphere at room temperature. After 3 h, the reaction solution was directly filtered through a pad of silica and condensed. The resulting residue was purified by radial chromatography (4 mm plate, 10% ethyl acetate/hexanes) yielding a mixture of enantiomers 8a and 8b as an off-white solid (0.72 g, 80%): Rf=0.46 in 10% ethyl acetate/hexanes; $^1$H-NMR (CDCl$_3$) δ 8.08–8.05 (m, 2H), 7.84–7.78 (m, 3H), 7.71 (bs, 1H), 7.58–7.41 (m, 4H), 7.35–7.29 (m, 2H), 7.24 (dd, 2H, J=5.7, 2.7), 7.07–7.04 (m, 1H), 6.92 (dd, 1H, J=6.3, 1.9), 4.88 (t, 1H, J=7.7), 2.83 (ddd, 1H, J=2.2, 7.7, 14.6), 2.69–2.60 (ddd, 1H, J=6.6, 7.98, 14.6).

Trans-3-(2-Naphthyl)indan-1-ol, 9a and 9b.

Trans-3-(2-Naphthyl)indan-1-benzoate esters, 8a and 8b (0.681 g, 1.87 mmol) were dissolved in THF (60 mL) and methanol (35 mL) was added. Aqueous potassium hydroxide (3M, 10 mL) was added and the reaction solution was stirred vigorously at room temperature for 1.5 h until no starting material was detected by TLC. The methanol was removed in vacuo and the remaining solution was acidified to pH=3 with 3 M HCl (aq). The aqueous solution was extracted with ether (3×50 mL) and the combined organic layers were concentrated in vacuo. The residue was purified by radial chromatography (4 mm plate, 30% ethyl acetate/hexanes) to provide the enantiomers 9a and 9b as a clear oil (0.347 g, 71%) which foamed under high vacuum: $R_f$=0.37 in 30% ethyl acetate/hexanes; $^1$H-NMR (CDCl$_3$) δ 7.89–7.73 (m, 3H), 7.59 (bs, 1H), 7.50–7.41 (m, 3H), 7.32–7.15 (m, 3H), 5.40 (dd, 1H, J=3.0, 6.3), 4.77 (t, 1H, J=7.4), 2.58 (ddd, 1H, J=2.8, 7.7, 13.8), 2.45 (ddd, 1H, J=6.3, 7.2, 13.8), 2.14 (bs, 1H).

Trans-1-Methoxy-3-(2-napththyl)indans, 10a and 10b.

Sodium hydride (64.0 mg, 1.60 mmol) and methyl iodide (95.0 µL, 1.53 mmol) were added to a solution of trans-3-(2-naphthyl)indan-1-ols 9a and 9b (0.100 g, 0.384 mmol) at room temperature. The reaction was stirred under a nitrogen atmosphere for 16 h. The reaction was quenched with excess water (25 mL), then extracted with ether (3×25 mL). The combined ethereal phases were condensed to provide a yellow oil that solidified under vacuum. The crude solid was purified by flash chromatography (12 g silica, 10% ethyl acetate/hexanes) to afford the enantiomers 10a and 10b as a pale yellow oil (82 mg, 78%): $R_f$=0.47 in 10% ethyl acetate/hexanes; $^1$H-NMR (CDCl$_3$) δ 7.80–7.74 (m, 3H), 7.65 (bs, 1H), 7.51–7.41 (m, 3H), 7.30–7.17 (m, 3H), 7.01–6.98 ( m, 1H), 4.92 (dd, 1H, J=1.7, 5.8), 4.76 (t, 1H, J=8.0), 3.43 (s, 3H), 2.70 (ddd, 1H, J=1.4, 7.43, 13.76), 2.34 (ddd, 1H, J=6.05, 7.7, 13.76). Anal. ($C_{20}H_{18}O$) C, H.

Ethyl 3-(2-bromophenyl)-3-(3,4-dichlorophenyl)-2-cyanopropanoate, (3:3,4-$Cl_2$Ph).

Magnesium (0.30 g, 12.3 mmol) was added into a solution of 1,2-dichloro-4-bromobenzene (2.76 g, 12.2 mmol) in ether (6 mL) and the reaction was stirred for 3h. A solution of ethyl 2-cyano-3-(2-bromophenyl)-2-propenoate (3 g, 9.15 mmol) in toluene (6 mL) was added into the reaction mixture via an addition funnel over 15 min. The reaction mixture was then heated to 90° C. and stirred for 45 min. Ether was collected by Dean—Stark trap. The reaction mixture was poured into ice containing conc. $H_2SO_4$ (1 mL). The $H_2O$ layer was extracted with ether (3×40 mL). Ether was removed on a rotary evaporator affording the crude product as a yellow oil (4.49 g, quantitative): $R_f$ 0.32 (10% EtOAc/hexanes); $^1$H-NMR (CDCl$_3$) □ 7.57–7.63 (m, 7H), 5.24 (dd, 1H, J=8, 8 Hz), 4.11–4.29 (m, 31H), 1.16 (ddd, 3H, J=7, 7, 14 Hz).

3-(2-Bromophenyl)-3-(3,4-dichlorophenyl)-propanoic Acid, (4:3,4-$Cl_2$Ph).

Ethyl 3-(2-bromophenyl)-3-(3,4-dichlorophenyl)-2-cyanopropanoate (4.49 g, 9.45 mmol) in glacial acetic acid (20 mL), conc. $H_2SO_4$ (10 mL) and $H_2O$ (10 mL) was refluxed at 100° C. for 24 h. The hot solution was poured into ice in a beaker. White powder was formed and extracted with EtOAc (3×50 mL). Removal of solvent afforded 3.2 g of an oily solid. The residue was stirred in 3N NaOH (20 mL) for 30 min. The $H_2O$ layer was extracted with CHCl$_3$ (3×30 mL) to remove any organic side-products. The $H_2O$ layer was then acidified to pH 5 with 3N HCl (10 mL). White solid precipitate was formed and collected by filtration through a sintered funnel. After drying in vacuo, the solid weighed 2.1 g (59%): $^1$H-NMR (CDCl$_3$)□ 7.56 (dd, 1H, J=8, 1 Hz), 7.27–7.37 (m, 3H), 7.08–7.19 (m, 3H), 4.96 (t, 1H, J=8 Hz), 2.95–3.11 (m, 2H).

3-(3,4-Dichlorophenyl)indanone, (5:3,4-$Cl_2$Ph).

n—BuLi (2.5 M in hexanes, 4.15 mL, 10.4 mmol) was added dropwise over 15 min into a solution of ethyl 3-(2-bromophenyl)-3-(3,4-dichlorophenyl)-propanoic acid (1.77 g, 4.73 mmol) in ether (23 mL) at –10° C. After the addition, the reaction was allowed to stir at 0° C. in an ice bath for 40 min. 3N HCl (3 mL) was added slowly followed by $H_2O$ (5 mL). The $H_2O$ layer was extracted with ether (3×30 mL). The solvent was removed on a rotary evaporator. The residue was purified by flash chromatography (20% EtOAc/hexanes) to give a white solid (0.6 g, 46%): mp 112–113° C.; $R_f$ 0.39 (20% EtOAc/hexanes); $^1$H-NMR (CDCl$_3$) □ 7.82 (d, 1H, J=8 Hz), 7.60 (ddd, 1H, J=8, 8, 1 Hz), 7.42–7.48 (m, 1H), 7.37 (d, 1H, J=8 Hz), 7.24–7.27 (m, 1H), 7.22 (d, 1H, J=2 Hz), 6.94 (dd, 1H, J=8, 2 Hz), 4.54 (q, 1H, J=4 Hz), 3.23 (dd, 1H, J=19, 8 Hz), 2.61 (dd, 1H, J=19, 4 Hz). Anal. ($C_{15}H_{10}Cl_2O$) C, H, Cl.

Cis-3-(3,4-Dichlorophenyl)indan-1-ol, (6:3,4-$Cl_2$Ph).

K-Selectride (1M in THF, 2.7 mL) was added dropwise into a solution of 3-(3,4-dichlorophenyl)indanone (0.36 g, 1.28 mmol) at 0° C. The reaction was allowed to stir at 0° C. for 3h. 3M NaOH (0.5 mL) was added slowly followed by the addition of 30% $H_2O_2$ (0.5 mL). Water (20 mL) was added and the water layer was extracted with ether (3×20 mL). Ether was removed on a rotary evaporator. The residue was purified by flash chromatography to give 0.32 g (88%) of 6 as a colorless oil: $R_f$ 0.43 (EtOAc/hexanes); $^1$H-NMR (CDCl$_3$) □ 7.48 (d, 1H, J=7 Hz), 7.38 (d, 1H, J=8 Hz), 7.32–7.35 (m, 1H), 7.29–7.30 (m, 1H), 7.24–7.26 (m, 1H), 7.07 (dd, 1H, J=8,2 Hz), 6.94 (d, 1H, J=8 Hz), 5.29 (q, 1H, J=7 Hz), 4.15 (t, 1H, J=8 Hz), 3.01 (qd, 1H, J=7, 8 Hz), 2.06 (d, 1H, J=7 Hz), 1.88 (qd, 1H, J=7, 9 Hz). Anal. ($C_{15}H_{12}OCl_2$) C, H, Cl.

Cis-1-Methoxy-3-(3,4-dichlorophenyl)indans, (7:3,4-$Cl_2$Ph).

Sodium hydride (60% dispersion, 10 mg, 0.251 mol) was added into a solution of methyl iodide (16 mg, 0.25 mmol) and cis-3-(3,4-dichlorophenyl)indan-1-ol (35 mg, 0.125 mmol) in THF (1 mL). The mixture was stirred for 4 h. 3N HCl (1 mL) and $H_2O$ (5 mL) were added and the water layer was extracted with ether (3×1.0 mL). Ether was removed on a rotary evaporator. The residue was purified by flash chromatography (10% EtOAc/hexanes) to afford 18 mg (49%) of 7 as a colorless oil: $R_f$ 0.71 (20% EtOAc/hexanes); $^1$H-NMR (CDCl$_3$) □ 7.46–7.49 (m, 1H), 7.23–7.38 (m, 4H), 1.07 (dd, 1H, J=8, 2 Hz), 6.93–6.96 (m, 1H), 4.90 (t, 1H, J=6 Hz), 4.17 (t, 1H, J=8 Hz), 2.94 (qd, 1H, J=7, 6 Hz), 1.96 (qd, 1H, J=7, 6 Hz). Anal. ($C_{16}H_{14}OCl2$) C, H.

Benzoic Acid 3-phenylindan-1-yl ester, (8:3,4-$Cl_2$Ph).

Cis-3-(3,4-Dichlorophenyl)indan-1-ol (50 mg, 0.18 mmol), triphenylphosphine (0.100 g, 0.376 mmol), diethyl azodicarboxylate (0.06 mL, 0.358 mmol) and benzoic acid (44 mg, 0.358 mmol) in THF were stirred overnight. The organic solvent was removed on a rotary evaporator. The residue was purified by flash chromatography (10% EtOAc/hexanes) to afford 50 mg (73%) of 8 as a colorless oil: $R_f$ 0.63 (20% EtOAc/hexanes); $^1$H-NMR (CDCl$_3$) □ 8.02–8.05 (m, 2H), 7.51–7.63 (m, 2H), 7.25–7.47 (m, 6H), 7.00–7.05 (m, 1H), 6.55 (dd, 1H, J=6, 2 Hz), 4.66 (t, 1H, J=8 Hz), 2.78 (qd, 1H, J=7, 2 Hz), 2.47 (qd, 1H, J=7, 7 Hz).

Trans-3-(3,4-Dichlorophenyl)indan-1-ol, (9:3,4-$Cl_2$Ph).

Potassium hydroxide (3M, 1mL) was added into a solution of benzoic acid 3-phenyl-indan-1-yl ester (50 mg, 0.131 mmol) in methanol (2 mL) and THF (2 mL). The reaction mixture was stirred for 2 h. 3M HCl (0.5 mL) was added dropwise until pH=3.0, followed by the addition of $H_2O$ (5 mL). The $H_2O$ layer was extracted with ether (3×20 mL) to afford an oil (47 mg) $R_f$ 0.63 (20% EtOAc/hexanes). The crude oil was used in the next step without further purification.

Trans-1-Methoxy-3-(3,4-dichlorophenyl)indans, (10:3,4-$Cl_2$Ph).

Sodium hydride (60% dispersion, 26 mg, 0.674 mmol) was added into a solution of trans-3-(3,4-dichlorophenyl)indan-1-ol (47 mg, 0.168 mmol) and CH$_{31}$I (42 □L, 0.674 mmol) in THF (2 mL). The reaction mixture was stirred overnight. $H_2O$ (5 mL) was added and the $H_2O$ layer was extracted with ether (3×20 mL). The organic solvent was removed on a rotary evaporator. The residue was purified by flash chromatography (10% EtOAc/hexanes) to afford mg (50%) of a colorless oil: $R_f$ 0.50 (10% EtOAc/hexanes); $^1$H-NMR (CDCl$_3$) □ 7.44–7.48 (m, 1H), 7.36 (d, 1H, J=8 Hz), 7.25–7.32 (m, 2H), 7.23 (d, 1H, J=2 Hz), 6.96–7.00 (m, 2H), 4.87 (dd, 1H, J=6, 2 Hz), 4.55 (t, 1H, J=8 Hz), 3.41 (s, 3H), 2.65 (td, 1H, J=7, 2 Hz), 2.18 (qd, 1H, J=7, 8 Hz). Anal. (Cl$_6$H$_{14}$OCl$_2$) C, H, Cl.

II. SYNTHESIS OF TETRAHYDROPYRANYL ESTERS

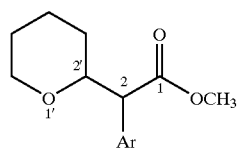

2-ARYL TETRAHYDROPYRAN-2-YL ACETIC ACID METHYL ESTERS (FOUR ENANTIOMERS)

In general, synthesis of the 2-aryl substituted tetrahydropyran-2-yl acetic acid methyl esters can be accomplished via an identical route to that presented below for the 2-(3,4-dichlorophenyl) analogs.

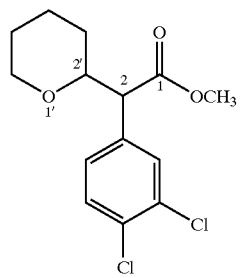

2-Chlorotetrahyropyran, prepared by passing hydrogen chloride gas into a solution of 2,3-dihydrotetrahydropyran in ether [Ficini, *J. Bull. Soc. Chim. Fr.* 119–124 (1956)], was reacted with the enolate of the appropriate methyl arylacetates to provide the desired product, exemplified below as a mixture of 1 and 2, in 77% yield (see Scheme 1).

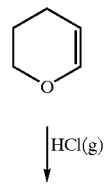

The product possesses two chiral centers (2, 2') and consequently there is a pair of enantiomers for each diastereomer. Therefore there exist four isomers as shown in Scheme 2 (Compounds 1 and 2).

Scheme 2

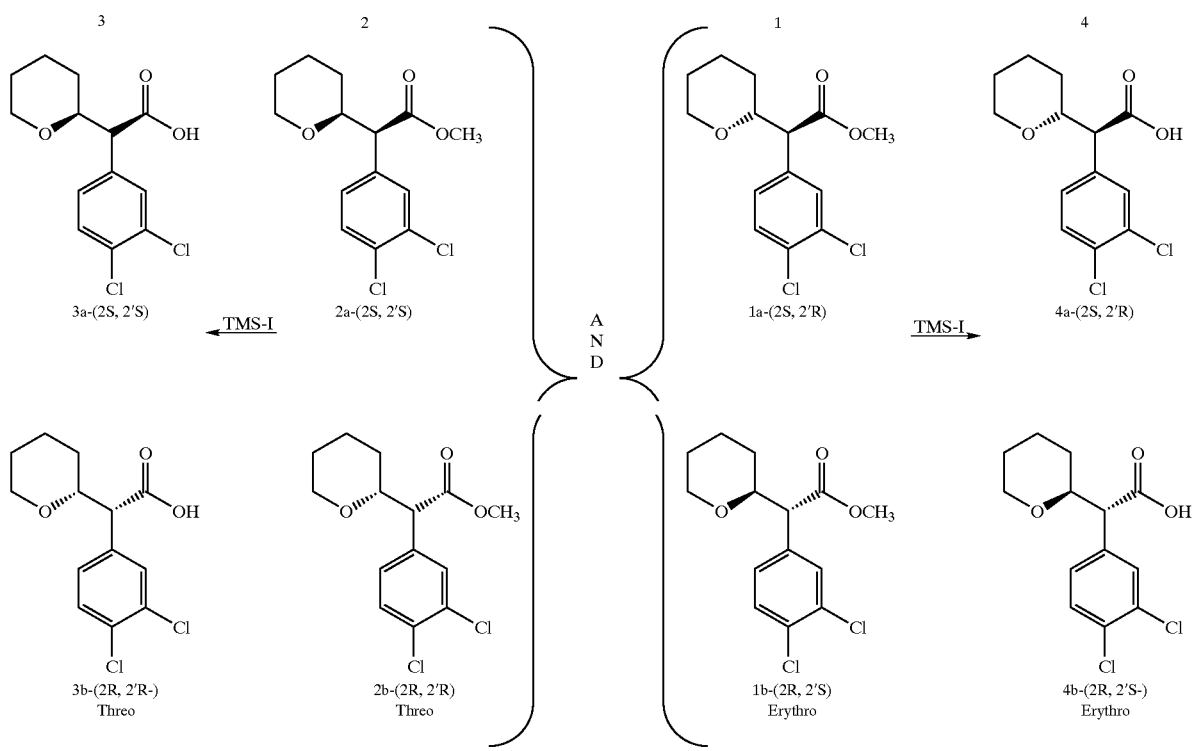
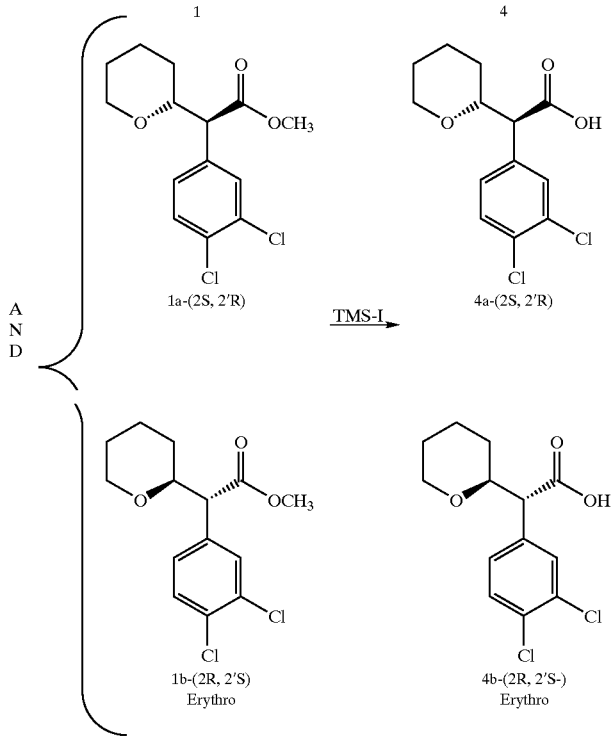

The product mixture (1 and 2) obtained from the reaction of 2-chlorotetrahyropyran with the enolate of methyl 3,4-dichlorophenylacetate presented as two spots on TLC in a ratio of 1.0:1.4 ($^1$H-NMR). These two spots represent the two diastereomeric pairs of enantiomers 1 (1a and 1b) and 2 (2a and 2b).

The two diastereomers 1 and 2 were separated by column chromatography to obtain diastereomer 1 as an oil (2S,2'R and 2R,2'S) and diastereomer 2 as a solid (2S,2'S and 2R,2'R). (The assignment of chirality was achieved by X-ray crystallographic analysis, see later). These pairs of methyl esters 1 and 2 were then hydrolyzed to their acids 4 and 3 respectively. To avoid epimerization, a neutral reagent, trimethylsilyl iodide (TMS-1), was used (W. P. Weber, Silicon Reagents for Organic Synthesis, Springer-Verlag, Berlin, Heidelberg, N.Y., 1983, page 30–31).

The enantiomeric acid pair (3a and 3b: S,S- and R,R-) resulting from hydrolysis of 2 was then transformed (Scheme 3) into diastereomeric menthyl esters (5a and 5b) by treatment of their acid chlorides with optically pure L-menthol. Careful column chromatography then allowed separation of the two newly formed diastereomeric menthyl esters 5a and 5b. These two diastereomerically pure menthyl esters were each separately hydrolyzed (TMS-1) to give the two optically pure acids 3a and 3b.

One of the acids (3a) was crystallized and its absolute configuration was determined by X-ray crystallography. Thus the configuration of 3a was proved to be 2S,2'S. Therefore 3b was proved to be the 2R,2'R enantiomer.

Acids 3a and 3b were then methylated with trimethylsilyl diazomethane to furnish optically pure target molecules 2a-(2S,2'S) (O-1794) and 2b-(2R,2'R) (O-1783).

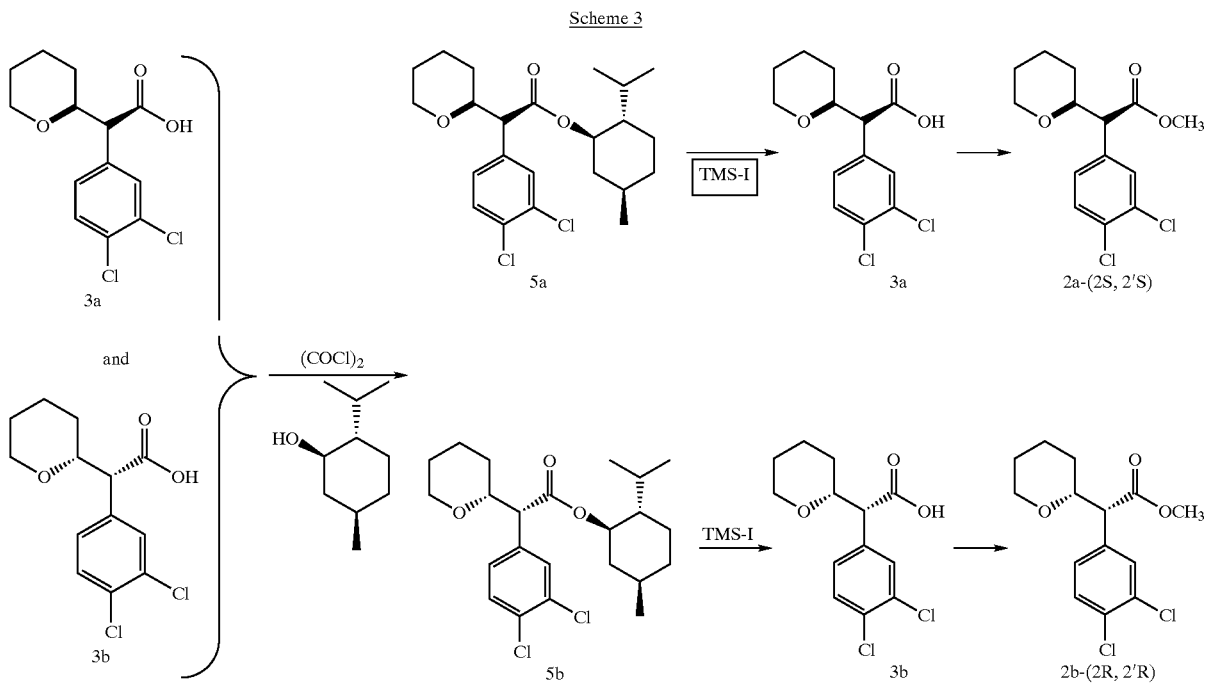

Scheme 3

In contrast, the menthol esters of the diastereomeric pair of acids 4a and 4b proved difficult to separate by column chromatography.

Therefore to obtain the remaining two isomers 1a-(2S, 2'R) and 1b-(2R,2'S), the racemic acids (as a mixture of 4a and 4b) from hydrolysis of the mixed methyl esters [1a-(2S, 2'R) and 1b-(2R,2'S)] were converted (Scheme 4) to the diastereomeric indanyl esters (6a and 6b) by reaction of their acid chlorides with (S)-(+)-1-indanol. The two indanyl esters were resolved by medium pressure flash column chromatography (AR$_f$<0.02). They were then each separately hydrolyzed with trimethylsilyl iodide to provide the two optically pure acids 4a and 4b and methylated with trimethylsilyl diazomethane to furnish the enantiomerically pure methyl esters 1a-(2S,2'R) and 1b-(2R,2'S).

One of the optically pure acids thus obtained (4b) was reacted, via its acid chloride, with p-nitrophenol to obtain the p-nitrophenylester. This compound was then recrystallized and X-ray crystallographic analysis of this p-nitrophenylester derivative then confirmed its configuration as 2R,2'S. Therefore the methyl ester derived from acid 4b is compound 1b-(2R,2'S) (O-1792). Therefore the remaining enantiomer is 1a-(2S,2'R) (O-1793).

Scheme 4

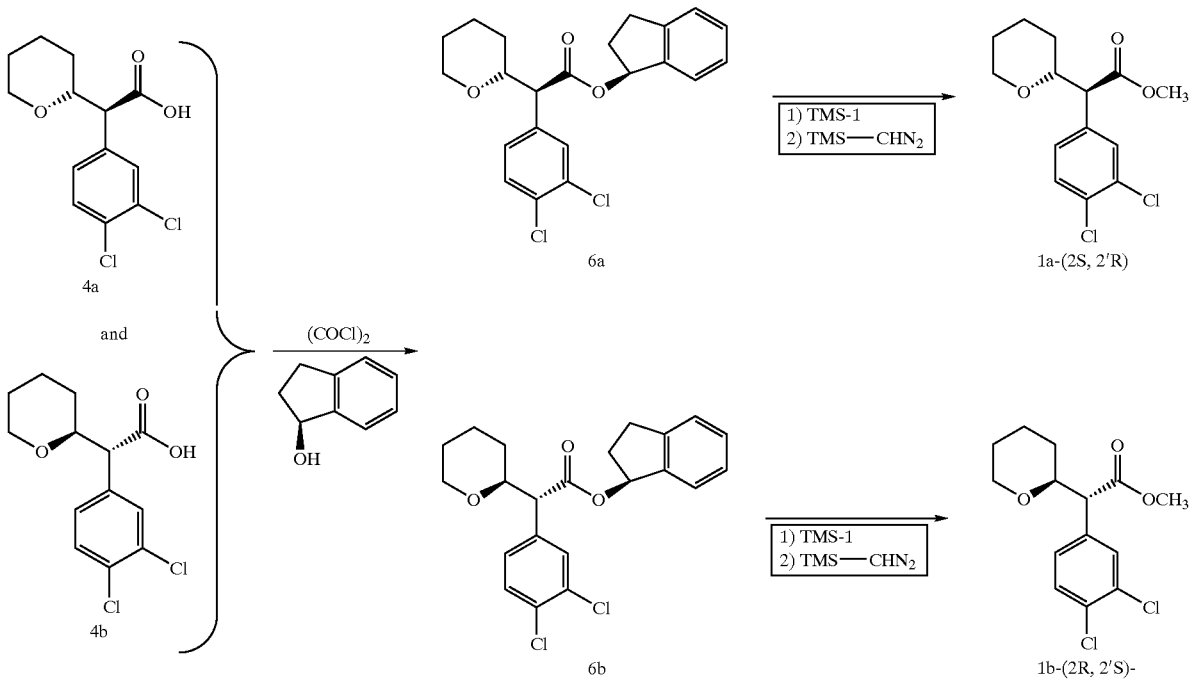

Summary Binding Data for the Methyl Ester Isomers

| Compound | Number | DAT IC$_{50}$ (nM) | SERT IC$_{50}$ (nM) |
|---|---|---|---|
| O-1793 l-erythro | 1a-(2S, 2'R) | 736 ± 59 | >10,000 |
| O-1792 d-erythro | 1b-(2R, 2'S) | 193 ± 3.5 | >10,000 |
| O-1794 l-threo | 2a-(2S, 2'S) | 34 ± 8.6 | 1,655 ± 317 |
| O-1783 d-threo | 2b-(2R, 2'R) | 17 ± 1.3 | >10,000 |

DAT = Inhibition of WIN 35,428 binding to the dopamine transporter
SERT = Inhibition of citalopram binding to the serotonin transporter

Table of Data for Four Enantiomeric Acids

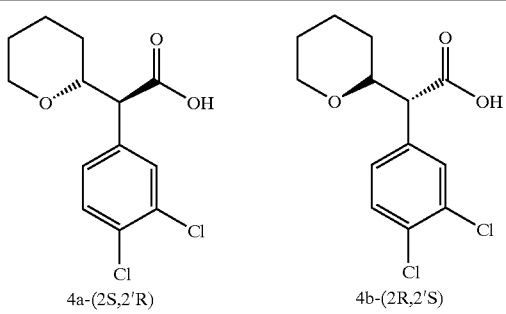

| Number | 4a | 4b | 3a | 3b |
|---|---|---|---|---|
| Configuration | 2S,2'R | 2R,2'S | 2S,2'S | 2R,2'R |
| Melting point ° C. | 124.2–125.2 | 124.1–125.1 | 138.9–139.9 | 139.1–140 |
| [α]$_D^{20}$ (c = 1, CHCl$_3$) | +14.0° | −13.9° | +18.8° | −19.1° |

Experimental Section

NMR spectra were recorded in CDCl$_3$ on a JEOL 300 NMR spectrometer operating at 300.53 MHz for $^1$H, and 75.58 MHz for $^{13}$C. TMS was used as internal standard. Melting points are uncorrected and were measured on a Gallenkamp melting point apparatus. Thin layer chromatography (TLC) was carried out on Baker Si250OF plates. Visualization was accomplished with either UV exposure or treatment with phosphomolybdic acid (PMA). Flash chromatography was carried out on Baker Silica Gel 40 mM. Elemental analyses were performed by Atlantic Microlab, Atlanta, Ga. All reactions were conducted under an inert (N$_2$) atmosphere.

2-Chlorotetrahydropyran.

Dry HCl gas was bubbled through a solution of 3,4-dihydro-2H-pyran (34.1 g, 0.41 mol) in 150 mL of anhydrous ether cooled in a dry-ice/acetone bath for ca. 2 h. Ether was removed by evaporation and fractional distillation of the residue under reduced pressure (bp 36–39° C./18 Torr) furnished 36.75 g (0.31 mol, 75%) of colorless oil. 1H-NMR (CDCl$_3$) δ 1.4–1.8 (m, 3H), 1.9–2.2 (m, 3H), 3.7–3.8(m, 1H), 3.9–4.1 (m, 1H), 6.27 (t, J=0.54 Hz, 1H). This compound was used immediately in the next step.

2-(3,4-Dichlorophenyl)tetrahydropyran-2-yl Acetic Acid Methyl Esters, 1 and 2.

n—Butyl lithium (Aldrich, 2.5 M in hexane) (20.8 mL, 52 mmol) was added dropwise to a solution of diisopropylamine (4.8 g, 48 mmol) in anhydrous diethyl ether (100 mL). After stirring at 0° C. for 1.5 h (yellow solution), methyl 3,4-dichlorophenylacetate (9.6 g, 44 mmol) in THF (20 mL) was added dropwise over 30 min; the solution became black. After completion of addition, the solution was stirred for a further 2 h. The round-bottom flask was then immersed in a dry-ice-acetone bath (–78° C.) and the mixture stirred for an additional 20 min.

The mixture was then added dropwise to a solution of 2-chlorotetrahydropyran (5.3 g, 44 mmol) in 40 mL of THF over 1 h and then slowly warmed to room temperature and stirred overnight. Cold (0° C.) 0.5 N hydrochloric acid (104 mL) was added, followed by 400 mL of ethyl acetate. The layers were separated and the organic layer was washed with brine and dried over anhydrous sodium sulfate.

TLC showed two major spots, both of which were UV and PMA active in a ratio of 1:1.4 based on $^1$H-NMR.

The crude product was purified by column chromatography using gradient ethyl acetate in hexane (5–15% of ethyl acetate). Total yield was 54%. The first products 1 were obtained as an oil (2.97 g): R$_f$=0.59 (20% ethyl acetate in hexane); $^1$H-NMR (CDCl$_3$) δ 7.47 (d, J=2.2 Hz, 1H), 7.38 (d, 8.5 Hz, 1H), 7.21 (dd, J=2.2, 8.5 Hz, 1H), 3.93–3.80 (m, 2H), 3.67 (s, 3H), 3,35 (d, J=11.5 Hz, 1H), 3.40–3.26 (m, 1H), 1.90–1.20 (m, 6H). $^{13}$C-NMR 171.74, 136.61, 132.37, 131.56, 130.97, 130.26, 128.49, 78.22, 68.95, 56.94, 52.33, 31.67, 29.97, 25.72, 23.24. The second products 2 were obtained as a solid (4.27 g): R$_f$=0.50 (20% ethyl acetate in hexane); mp 65° C.; $^1$H-NMR (CDCl$_3$) δ 7.47 (d, J=1.9 Hz, 1H), 7.38 (d, J=8.3 Hz, 1), 7.19 (dd, J=1.9, 8.3 Hz, 1H), 3.99 (dt); $^{13}$C-NMR 172.69, 135.45, 132.83, 132.07, 130.63, 128.18, 79.24, 68.91, 57.41, 52.36, 29.16, 25.72, 23.13.

2-(3,4-Dichlorophenyl)tetrahydropyran-2-yl Acetic Acids, 3a and 3b.

The combined methyl esters 2 (8.5 g, 28 mmol) were dissolved in anhydrous chloroform (10 mL) at room temperature. Trimethylsilyl iodide (14 g, 70 mmol, 2.5 equiv.) was added dropwise with stirring. The mixture was heated at 8° C. overnight. It was then cooled to room temperature and the volatiles were evaporated. Aqueous sodium thiosulfate solution (1%) and 25 mL of diethyl ether were added to the residue and the two layers were separated. The colorless ether phase was dried over sodium sulfate, filtered, and concentrated. The residue was purified by column chromatography (30% ethyl acetate in hexane, then 50% ethyl acetate in hexane). The acids 3a and 3b were obtained (5.2 g, 65% combined yield). $^1$H-NMR (CDCl$_3$) δ 7.43 (d, J=2.2 Hz, 1H), 7.40 (d, J=8.5 Hz, 1H), 7.21 (dd, J=8.3, 2.2 Hz, 1H), 3.98 (dd, J=10.8, 2.3 Hz, 1H), 3.87 (m, 1H), 3.61 (d, J=7.4 Hz, 1H), 3.4 (m, 1H), 1.95–1.20 (m, 6H).

2-(3,4-Dichlorophenyl)tetrahydropyran-2-yl Acetic Acid Menthyl Esters, 5a and 5b.

The combined 3,4-dichlorophenyl tetrahydropyran-2-yl acetic acids 3a and 3b (0.86 g, 3.0 mmol) were dissolved in 80 mL of anhydrous dichloromethane. Three drops of DMF were added, followed by the dropwise addition of oxalyl chloride (0.58 g, 4.8 mmol, 1.6 equiv.) at room temperature. The solution was stirred for 3 h. Volatiles were removed and anhydrous THF (75 mL) was introduced followed by the addition of pyridine (0.5 g). L-Menthol (0.47 g, 3.0 mmol) in THF (5 mL) was added dropwise. The reaction mixture was stirred overnight and then poured into 100 mL of water. Ether (150 mL) was added. The layers were separated and the aqueous phase was further extracted with ether. The combined organic phase was washed with brine and dried over sodium sulfate, filtered and concentrated.

TLC (10% ethyl acetate in hexane) showed two major spots (R$_f$ 0.54 and 0.50). After column chromatography (hexane 800 mL, 1% ethyl acetate in hexane 800 mL, and finally 3% ethyl acetate 800 mL), 400 mg of the first product 5a: R$_f$=0.54 (10% ethyl acetate/hexanes); $^1$H-NMR (CDCl$_3$) 7.50 (d, J=2.19 Hz, 1H), 7.38 (d, J=8.25 Hz, 1H), 7.22 (dd, J=2.19, 8.25 Hz, 1H), 4.70 (td, J=4.38, 11.04 Hz, 1H), 3.94 (dt, J=2.19, 11.28 Hz, 1H), 3.79 (td, J=2.19, 10.44 Hz, 1H), 3.45 (td, J=2.73, 9.06 Hz, 1H), 3.46 (d, J=9,87 Hz, 1H), 2.0–0.9 (m, 15H), 0.88 (d, J=7.68 Hz, 3H), 0.86 (d, J=6.6 Hz, 3H), 0.72 (d, J=6.87 Hz, 3H); $^{13}$C-NMR (CDCl$_3$) 171.76, 135.69, 132.55, 131.70, 130.55, 130.37, 120.21, 79.39, 74.93, 68,53, 57.83, 47.03, 40,53, 34.20, 31.37, 28.96, 25.70, 23.07, 21.96, 20.86, 15.86; and 425 mg of a second product 5b was obtained (65% combined yield): R$_f$=0.50 (10% ethyl acetate/hexanes); $^1$H-NMR (CDCl$_3$) 7.47 (d, J=2.19 Hz, 1H), 7.38 (d, J=8.22 Hz, 1H), 7.20 (dd, J=2.19, 8.22 Hz, 1H), 4.68 (td, J=4.41, 10.98 Hz, 1H), 3.94 (dt, J=2.19, 11.25 Hz, 1H), 3.83 (td, J=2.19, 10.17 Hz, 1H), 3.44 (td, J=3.03, 12.10 Hz, 1H), 3.45 (d, J=9.90 Hz, 1H), 2.0–0.9 (m, 15H), 0.88 (d, J=6.66 Hz, 3H), 0.78 (d, J=6.87 Hz, 3H), 0.61 (d, J=6.87 Hz, 3H); $^{13}$C-NMR (CDCl$_3$) 171.15, 135.76, 132.56, 131.72, 130.52, 130.42, 128.08, 78.86, 75.03, 68,61, 58.27, 47.15, 40,72, 34.21, 31.40, 29.02, 25.79, 25.62, 23.23,.23.07, 21.96, 20.67, 15.91.

2-(3,4-Dichlorophenyl)tetrahydropyran-2-yl Acetic Acid, 4a and 4b.

The methyl ester 1 (4.4 g, 14.5 mmol) was dissolved in anhydrous chloroform (60 mL) and Me$_3$SiI (10.0 g) was added. The mixture was heated in an oil bath at 80° C. After 20 h, $^1$H-NMR showed the reaction was only 25% complete. The reaction mixture was then heated for an additional 4 days whereupon it was cooled to room temperature and ice (20 g) was added, followed by addition of Na$_2$SO$_3$ solution (0.5N) to the point that almost no red color remained. The layers were separated and the: aqueous phase was extracted with CH$_2$Cl$_2$ (80 mL×2). The combined organic extracts were dried over Na$_2$SO$_4$. The crude product was purified by column chromatography (200 g of silica gel, CH$_2$Cl$_2$, 3L, 3% MeOH in CH$_2$Cl$_2$, 3L) and 3.4 g of pure product, 4a and 4b, was obtained (83% yield). $^1$H-NMR (CDCl$_3$) δ 7.47 (d, J=2.19 Hz, 1H), 7.40 (d, J=8.52 Hz, 1H), 7.21 (dd, J=8.52, 2.19 Hz, 1H), 3.97 (dd, J=10.71, 2.22 Hz, 1H), 3.60 (d, J=7.14 Hz, 1H), 3.45–3.36 (m, 1H), 1.90–1.20 (m, 6H).

2-(3,4-Dichlorophenyl)tetrahydropyran-2-yl Acetic Acid Indanyl Esters, 6a and 6b.

The enantiomeric pair of 2-(3,4-dichlorophenyl) tetrahydropyran-2-yl acetic acids 4a and 4b (4.0 g, 13.83 mmol) was dissolved in anhydrous CH$_2$Cl$_2$ (80 mL) and 4 drops of DMF were added. Oxalyl chloride (3.5 g, 27.7 mmol, 2 equiv.) was added dropwise while the solution was vigorously stirred. Evolution of bubbles was observed. After completion of addition, the light yellow solution was stirred at room temperature for a further 2.5 h.

Solvent was removed by evaporation and the residue was dried in vacuo. (S)-(+)-1-Indanol (1.87 g, 13.9 mmol) was dissolved in anhydrous THF (25 mL) and dry pyridine (25 mL) and cooled to 0° C. The acid chloride, prepared as above, in THF (50 mL) was added dropwise to this cold, stirred solution and stirred at 0° C. for 2 h, and then warmed up to room temperature and stirred overnight. $^1$H-NMR data show that the ratio of 6a ($R_f$=0.71 in 10% EtOAc, 90% hexane, developed 3 times) to 6b: ($R_f$=0.67) was 4:5 based on the peaks at 3.53 ppm and 3.54 ppm. The mixture was evaporated to remove most of the solvent. The residue was redissolved in a mixture of hexane/ethyl acetate (10:5) (80 mL) to provide a light yellow suspension. The mixture was loaded on a short silica gel pad and washed with hexane/ethyl acetate (10:1). The product fractions were combined and evaporated and dried. A light yellow oil was obtained (4.0 g, 71.4% crude yield). It was purified by column chromatography (300 g of silica gel, 0.4% of ethyl acetate, 99.6% of hexane, 4L, then 0.8% ethyl acetate in hexane, 5L). A total of 0.6 g of 6a, 1.0 g of a mixture of 6a and 6b, and 0.5 g of 6b were obtained. $^1$H-NMR (CDCl$_3$) 6a: δ 7.49 (d, J=2.19 Hz, 1H), 7.39–7.10 (m, 6H), 6.20 (m, 1H), 3.92–3.80 (m, 2H), 3.53 (d, J=8.79 Hz, 1H), 3.34–3.25 (m, 1H), 3.1–3.0 (m, 1H), 2.9–2.8 (m, 1H), 2.5–2.4 (m, 1H), 2.0–1.1 (m, 6H). $^{13}$C-NMR 171.07, 144.31, 140.56, 136.56, 132.19, 131.39, 130.90, 130.08, 129.04, 128.50, 126.73, 125.34, 124.85, 79.09, 78.16, 68.80, 57.08, 31.99, 30.13, 29.81.

6b: $^1$H-NMR (CDCl$_3$) δ 7.47 (d, J=2.19 Hz, 1H), 7.37 (d, J=8.25 Hz, 1H), 7.31–7.18 (m, 5H), 6.17 (m, 1H), 3.92–3.80 (m, 2H), 5.53 (d, J=8.52 Hz, 1H), 3.40–3.27 (m, 1H), 3.14–3.03 (m, 1H), 2.95–2.82 (m, 1H), 2.59–2.40 (m, 1H), 2.2–1.2 (m, 6H). $^{13}$C-NMR 171.09, 144.28, 140.37, 136.48, 132.16, 131.37, 130.95, 130.07, 129.05, 128.51, 126.72, 125.28, 124.82, 79.18, 78.16, 68.84, 57.04, 32.23, 30.15, 29.81, 25.61, 23.14.

Hydrolysis of Menthyl (5a and 5b) and Indanyl (6a and 6b) Esters (General Procedure)

The hydrolyses of the menthyl and indanyl esters to the corresponding acids was conducted similarly and yields were in a range of 38–55%. The procedure is exemplified for 6a below.

2S-(3,4-Dichlorophenyl)tetrahydropyran-2'R-yl Acetic Acid, 4a-2S,2'R.

The indanyl ester 6a (1.65 g, 4.07 mmol) was dissolved in anhydrous carbon tetrachloride (25 mL). Trimethylsilyl iodide (2.4 g, 12 mmol, 3 equiv.) was added. The mixture was heated at 90° C. with stirring for 18 h.

The reaction mixture was cooled to 0° C., cold water (20 mL) and dichloromethane (50 mL) were added and layers were separated. The aqueous phase was washed with dichloromethane (50 mL×2). The combined organic phases were dried over anhydrous sodium sulfate and filtered. The filtrate was evaporated to dryness. The residue was purified by column chromatography (10% methanol in dichloromethane) and 600 mg of product 4a was obtained (55% yield). Mp 124.2–125.2° C. $[\alpha]_D^{20}$=14.0° (c=1, CHCl$_3$); $^1$H-NMR (CDCl$_3$) δ 7.47 (d, J=2.19 Hz, 1H), 7.40 (d, J=8.52 Hz, 1H), 7.21 (dd, J=8.52, 2.19 Hz, 1H), 3.97 (dd, J=10.77, 2.22 Hz, 1H), 3.92–3.83 (m, 1H), 3.60 (d, J=7.14 Hz, 1H), 3.45–3.36 (m, 1H), 1.9–1.2 (m, 6H), 2R-(3,4-Dichlorophenyl)tetrahydropyran-2'S-yl Acetic Acid, 4b-2R,2'S.

Acid 4b was obtained from 6b as described above for 4a. $^1$H-NMR data are identical 4a. Mp 124.1–125.1° C.$[\alpha]_D^{20}$=−13.9° (c=1, CHCl$_3$). $^{13}$C-NMR(CDCl$_3$) 176.67, 135.53, 132.36, 131,80, 131.18, 130.21, 128.74, 77.82, 68.95, 56.60, 29.56, 25.49, 23.04

2S-(3,4-Dichlorophenyl)tetrahydropyran-2'S-yl Acetic Acid, 3a-2S,2'S.

Acid 3a was obtained from 5a as described for 4a above. M.p. 138.9–139.9° C. $[\alpha]_D^{20}$=18.8° (c =1, CHCl$_3$). $^1$H-NMR (CDCl$_3$) δ 7.45 (d, J=1.95 Hz, 1H), 7.40 (d, J=8.25 Hz, 1H), 7.18 (dd, J=8.25, 2.22 Hz, 1H), 4.06 (dt, J=11.22, 1.92 Hz, 1H), 3.9–3.7 (m, 11H), 3.52 (d, J=9.33 Hz, 1H), 3.50 (td, J=11.25, 3.3 Hz, 1H), 1.9–1.1 (m, 6H).

2R-(3,4-Dichlorolphenyl)tetrahydropyran-2'yl Acetic Acid, 3b-2R,2'R.

Acid 3b was obtained from 5b as described for 4a above. NMR data are identical to acid 3a. Mp 139.1–140.1° C. $[\alpha]_D^{20}$=−19.1° (c=1, CHCl$_3$)

2-(3,4-Dichlorophenyl)tetrahydropyran-2-yl Acetic Acid Methyl Esters, 1a, 1b, 2a, 2b (General Procedure)

Acids 3a, 3b, 4a, 4b, were methylated with trimethylsilyl diazomethane to obtain the methyl esters. The following procedure is representative.

2S-(3,4-Dichlorophenyl)tetrahydropyran-2'R-yl Acetic Acid Methyl Ester, 1a-2S, 2'R.

Acid 4a-2S, 2'R (90 mg, 0.31 mmol) was dissolved in anhydrous toluene (4 mL) and anhydrous methanol (1mL). Trimethylsilyl diazomethane (0.63 mL, 2.0M in hexane, 1.25 mmol, 4 equiv) was slowly added while stirring at room temperature and the mixture was stirred for 5 h. Volatiles were removed in vacuo. The residue (100 mg) was purified by column chromatography (2% ethyl acetate in hexane) to provide 1a-2S, 2'R as an of oil (61 mg, 64% yield). $^1$H-NMR (CDCl$_3$) δ 7.47 (d, J=2.19 Hz, 1H), 7.39 (d, J=8.25 Hz, 1H), 7.22 (dd, J=8.25, 2.19 Hz, 1H), 3.92–3.81 (m, 1H), 3.68 (s, 3H), 3.56 (d, J=8.52 Hz, 1H), 3.39–3.20 (m, 1H), 1.9–1.1 (m, 6H). Anal calcd. for C$_{14}$H$_{16}$O$_3$Cl$_2$=C 55.46, H 5.32, Cl 23.39; found: C 55.56, H 5.42, Cl 23.51.

2R-(3,4-Dichlorophenyl)tetrahydropyran-2'S-yl Acetic Acid Methyl Ester, 1b-2R, 2'S.

Methyl ester 1b was prepared from 4b as described above for 1a. $^1$H-NMR data identical to those of 1a. Anal. calcd. for C$_{14}$H$_{16}$O$_3$Cl$_2$: C 55.46, H 5.32, Cl 23.39; found: C 55.55, H 5.38, Cl 23.51.

2S-(3,4-Dichlorophenyl)tetrahydropyran-2'S-yl Acetic Acid Methyl Ester, 2a-2S, 2'S.

Methyl ester 2a was prepared from 3a as described above for 1a. $^1$H-NMR (CDCl$_3$) δ 7.48 (d, J=1.92 Hz, 1H), 7.39 (d, J=8.25 Hz, 1H), 7.25 (dd, J=8.25, 2.19 Hz, 1H), 4.03–3.95 (m, 1H), 3.84 (td, J=10.71, 2.19 Hz, 1H), 3.70 (s, 3H), 3.50 (d, J=9.9 Hz, 1H), 3.47 (td, J=11.34, 3.3 Hz, 1H), 1.9–1.0 (m, 6H). Anal. calcd. for C$_{14}$H$_{16}$O$_3$Cl$_2$: C 55.46, H 5.32, Cl 23.39; found: C 55.63, H 5.43, Cl 23.47, 2R-(3,4-Dichlorophenyl)tetrahydropyran-2'R-yl) Acetic Acid Methyl Ester, 2b-2R, 2'R.

Methyl ester 2b was prepared from 3b as described above for 1a. $^1$H-NMR data are identical to those of 2a. Anal. calcd. for C$_{14}$H$_{16}$O$_3$Cl$_2$: C 55.46, H 5.32, Cl 23.39, found: C 55.53, H 5.38, Cl 23.27.

2R-(3,4-Dichlorophenyl)tetrahydropyran-2'S-yl Acetic Acid p-nitrophenyl Ester, (p-Nitrophenyl Ester of 4b-2R, 2'S).

Compound 4b-(2R,2'S) obtained from 1b-(2R,2S') (100 mg) was dissolved in anhydrous dichloromethane (5 mL). One drop of DMF was added. Oxalyl chloride (0.14 g) was slowly added and the reaction mixture was stirred at room temperature for 3 h. Solvent was then removed by evaporation.

4-Nitrophenol (56 mg) was dissolved in anhydrous THF (3 mL) and pyridine (85 mg) was added. The mixture was cooled to 0° C. in an ice-water bath. To this cooled, stirred solution was added the acid chloride prepared above in 2 mL of THF over 10 min. The mixture was warmed up to room temperature and stirred overnight. The crude product was purified by column chromatography (0.6% ethyl acetate in hexane). The product (0.1 05 g) was obtained as a gummy material (75% yield). $R_f$=0.46 (20% ethyl acetate in hexane). $^1$H-NMR (CDCl$_3$) δ 8.3–8.2 (m, 2H), 7.55 (d, J=2.19 Hz, 1H), 7.45 (d, J=8.25 Hz, 1H), 7.32–7.18 (m, 3H), 4.07–3.91 (m, 2H), 3.83 (d, J=7.41 Hz, 1H), 3.46–3.37 (m, 1H), 2.0–1.2 (m, 6H). The gum was recrystallized from pentane. X-ray structural analysis showed the enantiomerically pure p-nitrophenyl ester of 4b to be of 2R,2'S configuration.

III. IN VITRO BINDING ASSAYS

The affinities and transporter selectivities of the drugs were assessed in brain tissue of adult cynomolgus or rhesus monkey (*Macaca fasicularis* or *Macaca Mulatta*). Caudate putamen was the source of the dopamine and serotonin transporters. The dopamine transporter affinity was measured with [3H]WIN 35,428 ([3H]CFT), the serotonin transporter was measured with [3H]citalopram and the norepinephrine transporter was measured with [3H]nisoxetine. Affinities of selected compounds were also measured at the human dopamine transporter in HEK-293 cells expressing the human dopamine transporter (hDAT).

A. Brain Tissue Preparation.

Brain tissue was harvested from adult male and female cynomolgus (Macaca fasicularis) or rhesus (Macaca Mulatta) monkeys euthanized in the course of other research or after spontaneous death. Tissue was stored in the brain bank at the New England Regional Primate Research Center at −85° C. The caudate-putamen (approximately 1.5 g) was dissected from coronal sections of brain. Each caudate-putamen was homogenized and used separately for dopamine and serotonin transporter assays. Prior to homogenization, the thalamus from two brains was pooled and membranes were prepared as described previously for norepinephrine transporter assays (Madras et. al., *Synapse*, 24:340–348, 1996). Briefly, the tissue was homogenized in 10 volumes (w/v) of ice-cold Tris.HCl buffer (50 mM, pH 7.4 at 0–4° C.) and centrifuged at 38,700×g for 20 min in the cold. The resulting pellet was resuspended in 40 volumes of buffer, and the entire wash procedure was repeated twice. The membrane suspension (25 mg original wet weight of tissue/ml) was diluted to 12 mg/ml in buffer just prior to assay and dispersed with a Brinkmanm polytron (setting #5) for 15 sec. Preliminary experiments demonstrated that tissue washing enhanced [$^3$H]WIN 35,428 (CFT) binding in tissue homogenates or tissue sections (Canfield et al., Synapse 6:189–194, 1990; Madras, et. al., *Mol. Pharmacol.* 36:518–524, 1989). All experiments were conducted in triplicate and each experiment was repeated in 2–4 individual tissue preparations.

B. Dopamine Transporter Assay to Measure Affinity of Candidate Compounds

Competition experiments to determine the affinities of drugs at [$^3$H]WIN 35,428 (CFT) binding sites at the dopamine transporter were conducted using procedures previously reported (Madras et al., *Mol. Pharmacol.* 36:518–524, 1989). Stock solutions of water-soluble drugs were dissolved in water or buffer and stock solutions of other drugs were made in a range of ethanol/HCl solutions. Several of the drugs were sonicated to promote solubility. The stock solutions were diluted serially in the assay buffer and added (0.2 ml) to the assay medium as described above. Each serial dilution in buffer was examined to ensure that the relatively water-insoluble compounds did not precipitate out. Affinities of drugs for the dopamine transporter were conducted as follows:

Affinities of drugs for the dopamine transporter, labeled by [$^3$H]CFT (Specific activity: approximately 80 Ci/mmol, NEN) were determined in experiments by incubating tissue with a fixed concentration of [$^3$H]CFT and a range of concentrations of unlabeled test drug. The assay tubes received, in Tris.HCl buffer (50 mM, pH 7.4 at 0–4° C.; NaCl 100 mM), at a final assay concentration: [$^3$H]CFT (1 nM, 0.2 ml); test drug (1 pM–100 μM, 0.2 ml or buffer), membrane preparation (0.2 ml, 1mg original wet weight of tissue/ml). The 2 h incubation (0–4° C.) was initiated by addition of membranes and terminated by rapid filtration over Whitman GFB glass fiber filters pre-soaked for 1 hour in 0.1% bovine serum albumin (Sigma Chem. Co.). The filters were washed twice with 5 ml Tris.HCl buffer (50 mM), incubated overnight at 0–4° C. in scintillation floor (Beckman Ready-Value, 5 ml) and radioactivity was measured by liquid scintillation spectrometry. Cpm were converted to dpm following determination of counting efficiency (49–53%) of each vial by external standardization. Total binding was defined as [$^3$H]CFT bound in the presence of ineffective concentrations of test drug (0.1–10 μM). Non-specific binding was defined as [$^3$H]CFT bound in the presence of an excess (30 μM) of (−)cocaine. Specific binding was the difference between the two values. In the caudate-putamn total binding of [$^3$H]CFT ranged from 1,500–3,500 dpm, and specific binding was approximately 90 % of total.

The affinity of([$^3$H]CFT) for the dopamine transporter was determined in experiments by incubating tissue with a fixed concentration of [$^3$H]CFT and a range of concentrations of unlabeled CFT. The assay tubes received, in Tris.HCl buffer (50 mM, pH7.4 at 0–4° C.; NaCl 100 mM), the following constituents at a final assay concentration: CFT, 0.2 ml (1 pM–100 or 300 nM), [$^3$H]CFT (0.3 nM); membrane preparation 0.2 ml (4 mg original wet weight of tissue/ml).

C. Serotonin Transporter Assay to Measure Affinity Candidate Compounds

The serotonin transporter was assayed in caudate-putamen membranes using similar assay conditions as for the dopamine transporter. The assays were conducted sideby-side to ensure that comparisons of the relative potencies of the drugs at the two transporters were similar. The affinity of drugs for the serotonin transporter labeled by [$^3$H]citalopram (spec. act.: approximately 85 Ci/mmol, NEN) was determined in experiments by incubating tissue with a fixed concentration of [$^3$H]citalopram and a range of concentrations of drug. Assays were conducted in Tris—HCl buffer containing NaCl (100 mM) and the following constituents: [$^3$H]citalopram (1 nM, 0.2 ml), test drug (1 pM–100 μM, 0.2 ml) and tissue (0.2 ml, 3 mg/ml original wet tissue weight). The 2 h incubation (0–4° C.) was initiated by addition of membranes and terminated by rapid filtration over Whatman GF/B glass fiber filters pre-soaked 1 hour in 0.1% polyethyleneimine. The filters were washed three times with 5 ml Tris.HCl buffer (5 0mM), and the remaining steps were carried out as described above. Total binding was defined as [$^3$H]citalopram bound in the presence of ineffective concentrations of unlabeled citalopram (1 pM) or the test compounds. Non-specific binding was defined as [$^3$H]citalopram bound in the presence of an excess (100 μM) of fluoxetine. Specific binding was the difference between the two values. Cpm were converted to dpm following determination of counting efficiency (>45%) of each vial by external standardization.

D. Norepinephrine Transporter Assay

The norepinephrine transporter was assayed in thalamus membranes using conditions similar to those for the serotonin transporter and adapted from whole rat brain (Gehlart et al., *J Neurochem.* 64:2792, 1995). The affinity of[$^3$H] nisoxetine (spec. act.: 74 Ci/mmol, NEN) for the norepinephrine transporter was determined in experiments by incubating tissue with a fixed concentration of [$^3$H]nisoxetine and a range of concentrations of unlabeled nisoxetine. The assay tubes received the following constituents at a final assay concentration: nisoxetine or drug (0.2 ml; 1 μM–300 μM), [$^3$H]nisoxetine (0.2 ml; 0.6 nM); membrane preparation (0.2 ml; 4 mg original wet weight of tissue/ml). The buffer in the assay medium was Tris—HCl: 50 mM, pH 7.4 at 0–4° C.; NaCl 300 mM. The 16 h incubation at 0–4° C. was initiated by addition of membranes and terminated by rapid filtration over Whatman GF/B glass fiber filters pre-soaked in 0.3% polyethyleneimine for 1 h. The remaining steps are described above. Total binding was defined as [$^3$H]nisoxetine bound in the presence of ineffective concentrations of drug. Non-specific binding was defined as [$^1$H]nisoxetine bound in the presence of an excess (10 μM) of desipramine. Specific binding was the difference between the two values.

E. Dopamine Transporter Assay in Cell Lines Expressing the Human Dopamine Transporter HDAT Cell Line (HEK-293) Preparation.

A full length human DAT cDNA isolated from a human substantia nigra cDNA library was ligated into pcDNA3.1 (InVitrogen), resulting in an human dopamine transporter expression vector, peDNA3.1/hDAT. HEK293 cells were grown in DMEM (BRL) supplemented with 10% fetal bovine serum (BR-L), 100U/ml penicillin, 100 μg streptomycin (BRL), and 0.1 mm non-essential amino acids (BRL), at 5% CO$_2$ in a 37° C. water-jacketed incubator. pcDNA3.1/hDAT (2 μg) was transfected into HEK-293 cells with Lipofectamine Reagent (BRL) according to the manufacturer's protocol. Following geneticin selection selection, single cells were replated into 12 well plates. At confluence, monoclonal cell lines were replated and assayed for [$^3$H].

The clone that displayed the highest dopamine uptake was selected and expanded for study of dopamine uptake.

Affinities of Drugs for Blocking [$^3$H]dopamine Transport in HEK-293cells Expressing the Human Dopamine Transporter (hDAT).

Low passage number cells (<25) plated at 80–90% confluency in 145 mm dishes were used for [$^3$H]dopamine transport studies. The medium was removed by aspiration, and cells were washed with Tris—Hepes buffer, pH 7.4 at 25° C. (Tris base: 5 mM, Hepes: 8.5 mM, NaCl: 120 mM, KCl: 5.4 mM, CaCl$_2$:1.2 mM, MgSO$_4$:1.2 mM and glucose: 10 mM. The cells were harvested, centrifuged at 125 g for 5 min, washed twice with the Tris—Hepes buffer and diluted to 1,250,000 cells/mi. The intact cell suspension (0.2 ml) was preincubated in triplicate with various drug dilutions for 1 5min. Dopamine transport was initiated by the addition of [$^3$H]dopamine (0.2 ml; DuPont-NEN, Boston, Mass.) for 10 min, at 25° C. The specific activity of the radioactive dopamine was 27.5 Ci/mM. Transport was terminated by filtration (Brandel, Gaithersburg, Md.) and two rapid washes with 5 ml of cold Tris-Hepes buffer over GF/B glass fiber filters (Whatman, Maidstone, UK) presoaked in 0.1% polyethylenimine (Sigma, St-Louis, Mo.). Bound radioactivity was measured by liquid scintillation (Wallac, Gaithersburg, Md.) spectrometry (LS60001C, Beckman, Fullerton, Calif.). Nonspecific uptake was defined as the uptake in the presence of 30 μM (−) cocaine, and these data were subtracted from total counts to yield specific accumulation of [$^3$]dopamine. The experiments were performed in triplicate and each value is the mean ±S.E. of 2–5 independent experiments. Protein concentrations were determined by Bradford assay (Bio—Rad, Richmond, Calif.).

Affinities of Drugs for the Dopamine Transporter, Labeled with [$^3$H]CFT in HEK-293 Cells Expressing the Human Dopamine Transporter.

Similar intact cell suspension (0.2 ml) in buffer with tropolone (100 μM) were used for [$^3$H]CFT binding studies. In triplicate, various dilution of drugs (0.2 ml; 10 pM to 10 μM) were incubated with 1 nM [$^3$H]CFT (0.2 ml; ≈80 Ci/mmol; NEN, Boston, Mass.) for 2 hours, at 4° C. Binding was terminated and measured as described above. Nonspecific binding was defined in the presence of 30 μM (−) cocaine, and these data were subtracted from total counts to yield total counts to yield specific binding of [$^3$H]CFT. The experiments were performed in triplicate and each value is the mean ±S.E. of 2-5 independent experiments. Competition analysis of [$^3$H]CFT binding was performed with EBDA and LIGAND computer programs (Elsevier-Biosoft, Cambridge, U.K.)

F. Data analysis.

Data were analyzed by the EBDA and LIGAND computer software programs (Elsevier-Biosoft, U.K.) Final estimates of IC$_{50}$ and nH values were computed by the EBDA program. Baseline values for the individual drugs were established by computer analysis, using the baseline drugs as a guide. The LIGAND program provided final parameter estimates for the affinity of the radioligand (Kd) by iterative non-linear curve-fitting and evaluation of one- or two-component binding models. LIGAND was used to measure the affinity of the radioligands at the dopamine and serotonin transporter. Graphs (not shown) were produced by the computer software program PRISM, using a one- or two-site competition analysis curve.

TABLE 1

Affinity of selected compounds at the dopamine and serotonin transporters

| COMPOUND | DAT IC$_{50}$ (nM) | SERT IC$_{50}$ (nM) | DAT/SERT RATIO |
|---|---|---|---|
| Methylphenidate | 17.2 ± 2.04 | >100,000 | 5,800 |
| 0-1730 (threo diastereomer) | 29.1 ± 5.05 | 2,180 ± 226 | 75 |
| 0-1731 (erythro diastereomer) | 286 ± 10.5 | 7,795 ± 1,840 | 27 |
| 0-1783; 2b | 17 ± 1.3 | >10,000 | >588 |
| 0-1792; 1b | 193 ± 3.5 | >10,000 | >50 |
| 0-1793; 1a | 736 ± 59 | >10,000 | >10 |
| 0-1794; 2a | 33.9 ± 8.6 | 1,655 ± 317 | 49 |
| Indatraline | 2.37 ± 0.11 | — | — |
| 0-1630 | 60 ± 23 | 334 ± 100 | 6 |
| Trans-geometry [3,4Cl$_2$Ph] | | | |
| 0-1618 | 104 ± 30.8 | >3,000 | >28 |
| 0-1629 | 116 ± 21 | >3,400 | >26 |
| 0-1617 | 130 ± 49.7 | >4,100 | >32 |
| Cis-geometry [3,4Cl$_2$Ph] | | | |
| 0-1833 | 189 ± 12 | 422 ± 38 | 2 |
| Cis-geometry [2-Naphthyl] | | | |
| 0-1925 | 213 ± 27 | 136 ± 4.5 | 0.6 |
| Trans-geometry [2-Naphthyl] | | | |
| O-2075 | 118 | 6,650 | 56 |
| O-2078 | 104 | 2,480 | 24 |
| O-2076 | 70 | >5000 | >70 |
| O-2089 | 755 | >10,000 | >13 |
| O-2098 | 25 | 1,400 | 56 |

A number of embodiments of the invention have been described. Nevertheless, it will be understood that various modifications may be made without departing from the spirit and scope of the invention. Accordingly, other embodiments are within the scope of the following claims.

What is claimed is:

1. A compound having the formula A, B, or C:

A
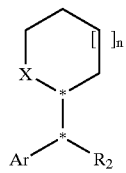

B
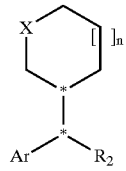

C
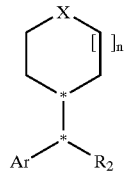

where
n is 1;
>X is >O;
—Ar=phenyl substituted at any two positions with $R_{1a}$ and $R_{1b}$, where $R_{1a}$ and $R_1b$ are as defined in options "I." or "II.", below;

OPTION I for $R_{1a}$, and $R_{1b}$
—$R_{1a}$ and —$R_{1b}$ are independently selected from:
—H; —Br; —Cl; —I; —F; —OH; —$OCH_3$; —$CF_3$; —$NO_2$; —$NH_2$; —CN; —$NHCOCH_3$, —$C(CH_3)_3$, —$(CH_2)_qCH_3$ where q=0–6; —$COCH_3$; —F (at the 2, 3 or 4 position), —Cl (at the 2, 3 or 4 position); —I (at the 2, 3 or 4 position); alkyl; alkenyl; alkynyl; allyl; iospropyl; isobutyl; alkyl; -alkyl$N_2S_2$ chelator; -alkyl$N_2S_2$Tc chelator; or $COR_4$, where $R_4$ is defined below;

OR

OPTION II, $R_{1a}$, and $R_{1b}$
—$R_{1a}$ and —$R_{1b}$ as a pair are independently selected from the following pairs: 3,4-diCl; 3,4, diOH; 3,4-diOAc; 3,4-di$OCH_3$; 3-OH,4-Cl; 3-OH,4-F; 3-Cl,4-OH, or 3-F,4-OH;

—$R_2$=—$COOCH_3$ or —$COR_1$; where,
—$R_1$ is —OH; —$CH_3$; —$CH_2CH_3$; —$CH_2(CH_2)_rCH_3$ where r=0, 1, 2, or 3; alkyl; alkenyl; alkynyl; allyl; isopropyl; iodoallyl; O-iodoallyl; or -isobutyl.

2. The compound of claim 1 in which the compound has a formula A.

3. The compound of claim 2 in which $R_2$=—$COR_4$.

4. The compound of claim 2 in which —Ar=phenyl substituted at any two positions with $R_{1a}$ and $R_{1b}$.

5. The compound of claim 4 in which $R_{1a}$ and $R_{1b}$ are independently selected from —H and —Cl.

6. The compound of claim 5 in which $R_{1a}$ and $R_{1b}$ are each —Cl.

7. A compound selected from the following compounds:
a) 2S-(3,4-Dichlorophenyl)tetrahydropyran-2'R-yl acetic acid methyl ester,
b) 2R-(3,4-Dichlorophenyl)tetrahydropyran-2'S-yl acetic acid methyl ester,
c) 2S-(3,4-Dichlorophenyl)tetrahydropyran-2'S-yl acetic acid methyl ester,
d) 2R-(3,4-Dichlorophenyl)tetrahydropyran-2'R-yl) acetic acid methyl ester,
e) 2S-(3,4-Dichlorophenyl)tetrahydropyran-2'R-yl acetic acid,
f) 2R-(3,4-Dichlorophenyl)tetrahydropyran-2'S-yl acetic acid,
g) 2S-(3,4-Dichlorophenyl)tetrahydropyran-2'S-yl acetic acid, and
h) 2R-(3,4-Dichlorophenyl)tetrahydropyran-2'R-yl acetic acid.

* * * * *